(12) United States Patent
Casar

(10) Patent No.: US 8,269,001 B2
(45) Date of Patent: Sep. 18, 2012

(54) PROCESS FOR THE SYNTHESIS OF HMG-COA REDUCTASE INHIBITORS

(75) Inventor: Zdenko Casar, Logatec (SI)

(73) Assignee: Lek Pharmaceuticals d.d., Ljublijana (SI)

( * ) Notice: Subject to any disclaimer, the term of this patent is extended or adjusted under 35 U.S.C. 154(b) by 1119 days.

(21) Appl. No.: 12/088,019

(22) PCT Filed: Oct. 4, 2006

(86) PCT No.: PCT/EP2006/009599
§ 371 (c)(1),
(2), (4) Date: Mar. 25, 2008

(87) PCT Pub. No.: WO2007/039287
PCT Pub. Date: Apr. 12, 2007

(65) Prior Publication Data
US 2008/0300406 A1   Dec. 4, 2008

(30) Foreign Application Priority Data
Oct. 5, 2005   (EP) .................................... 05021706

(51) Int. Cl.
*C07D 239/00* (2006.01)
*C07D 321/00* (2006.01)
(52) U.S. Cl. ...................................... 544/242; 549/200
(58) Field of Classification Search .................. 544/242; 549/200
See application file for complete search history.

(56) References Cited

U.S. PATENT DOCUMENTS
4,625,039 A   11/1986   Jewell, Jr. et al.
5,292,891 A   3/1994    Kaneko et al.

FOREIGN PATENT DOCUMENTS
WO   8600307     1/1986
WO   2005047276  5/2005

OTHER PUBLICATIONS

Ghorpade S R et al, Efficient synthesis of optically pure (4R,6S)-4-(-tert-butyldimethylsi lyloxy)-6-(hydroxymethyl) tetrahydropyran-2-one and its enantiomer, The Journal of Organic Chemistry, Oct. 5, 2001, pp. 6803-6806, vol. 66—No. 20.
Cattaneo D et al, Therapeutic use of HMG-CoA reductase inhibitors: Current practice and future perspectives, Expert Opinion on Therapeutic Patents, 2004, pp. 1553-1566, vol. 14—No. 11, United Kingdom.
Bennett F et al, Methyl (3R)-3-Hydroxyhex-5-Enoate, Journal of the Chemical Society, Perkin Transactions 1, Chemical Society, 1991, pp. 133-140, vol. 1.
Bennett F et al, Chiral Synthons for the Elaboration of Mevinic Acid Analogues, Tetrahedron Letters, 1988, pp. 4865-4868, vol. 29—No. 38.
Madrell S J et al, Nitrile Hydratase Enzymes in Organic Synthesis: Enantioselective Synthesis of the Lactone Moiety of the Mevinic Acids, Tetrahedron Letters, 1996, pp. 6001-6004, vol. 37—No. 33.
Kobayashi Y et al, Synthesis of Macrosphelides H and G, Tetrahedron Letters, 2002, pp. 4381-4384, vol. 43—No. 24.
Hareau G P-J et al, Synthesis of Optically Active 5-(tert-butyldimethylsiloxy)-2-Cyclohexenone and its 6-substituted derivatives as useful chiral building blocks for the synthesis of cyclohexane rings. Synthesis of Carvone, Penienone, and Penihydrone, Journal of the American Chemical Society, 1999, pp. 3640-3650, vol. 121—No. 15.
Cardillo G et al, Synthesis of Malyngolide and Antibiotic from the Marine Blue-Green Alga Lyngbya-Majuscula, Journal of Organic Chemistry, 1981, pp. 2439-2442, vol. 46—No. 12.

*Primary Examiner* — Paul V. Ward
(74) *Attorney, Agent, or Firm* — Luedeka Neely Group, P.C.

(57) ABSTRACT

A novel synthesis of statins uses Wittig reaction of a heterocyclic core of statin with a lactonized side chain already possessing needed stereochemistry. Any separation of diastereoisomers is performed early in the course of synthesis.

4 Claims, No Drawings

PROCESS FOR THE SYNTHESIS OF HMG-COA REDUCTASE INHIBITORS

This application is the National stage of International Application No. PCT/EP2006-009599, filed on Oct. 4, 2006, which claims benefit under 35 U.S.C. §119(e) of European Patent Application No. 05021706.6, filed on Oct. 5, 2005, the contents of both are incorporated herein by reference in their entirety.

FIELD OF THE INVENTION

The present invention relates to a process for the preparation of HMG-CoA reductase inhibitors, known also as statins, particularly to rosuvastatin. Specifically this invention relates to common intermediates which can be used for preparation of all statins.

BACKGROUND OF THE INVENTION

It is believed that the prerequisite for the biological activity of statins, of which the representative examples may be selected from rosuvastatin, cerivastatin, atorvastatin, fluvastatin, pitavastatin, bervastatin or their analogs or pravastatin, simvastatin, lovastatin or their analogs, is their structure, consisting of respectively a heptenoic or heptanoic acid moiety (free acid, salt or lactone) connected to the aromatic core and especially their stereochemistry, especially configuration at the chiral atoms as depicted in following formula of their representative example rosuvastatin anion:

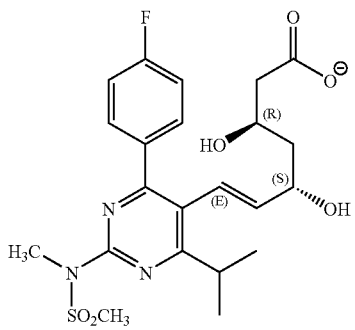

Synthetic approaches to statins are for example known from U.S. Pat. No. 4,625,039 and WO 05/047276.

DESCRIPTION OF THE INVENTION

In this invention a novel synthesis of statins is proposed wherein one center of chirality is present already in the readily available starting compound while the other is introduced early in the course of synthesis. We have thus developed a highly controlled process where the moiety IX possessing the desired stereochemistry:

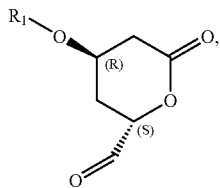

where $R_1$ is a protecting group;
is reacted with an appropriate phosphonium salt or phosphite of the skeleton of statin. It was important to synthesize this moiety from an (S) precursor in a stereoselective manner. This was achieved by reaction via new intermediate VII:

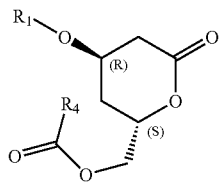

where $R_4$ is an (optionally substituted) alkyl.
So the only enantiomer separation step takes place when separating compounds:

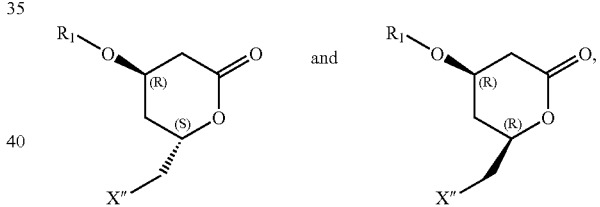

where X" is halo or alkyl- or arylsulfonyl; which is early in the course of synthesis. Furthermore we have been directing the synthesis of those precursor compounds in a manner to give high yield of the desired (4R,6S)-diastereoisomer.

The general synthetic route is depicted in following Scheme 1 and the specific example using silyl protection and is exemplified in the synthesis of rosuvastatin Ca in Scheme 2.

Scheme 1

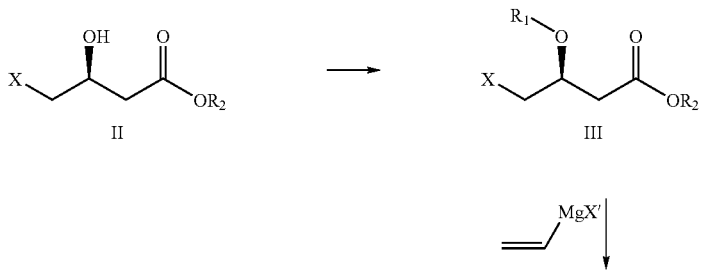

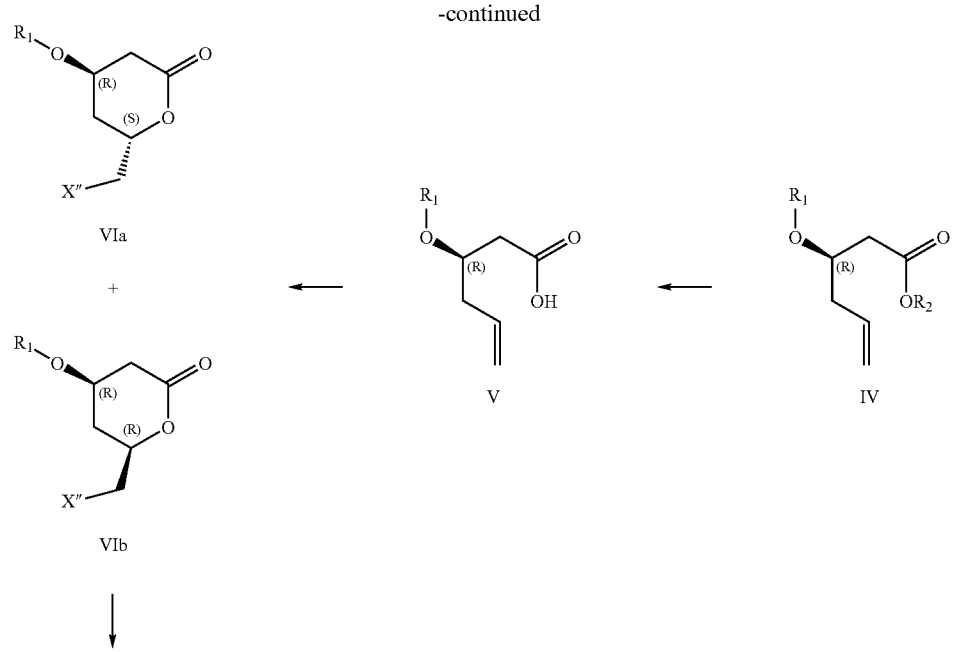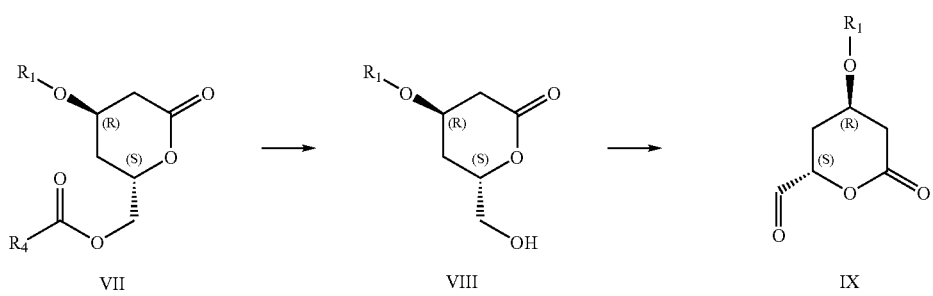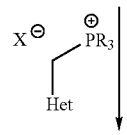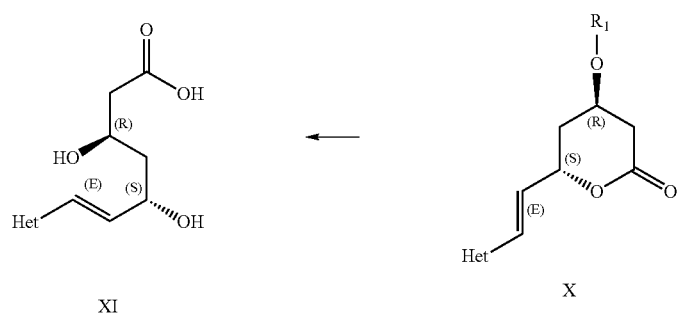

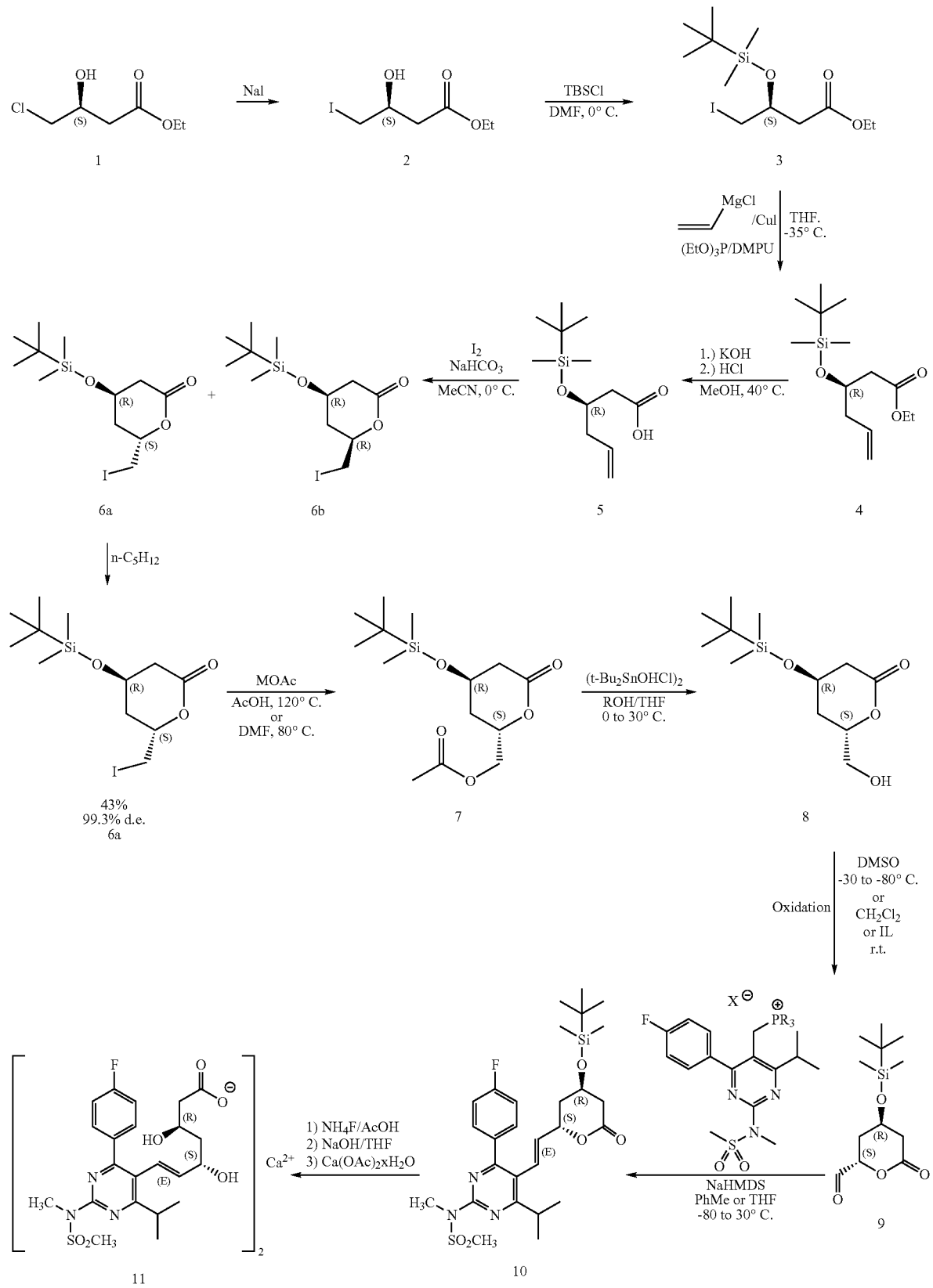
Scheme 2

In accordance with our invention, we react a compound IX:

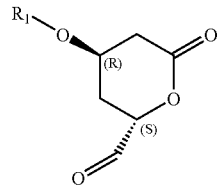

(where $R_1$ is a protecting group)

under condition of Wittig coupling with heterocylic derivatives of following formula:

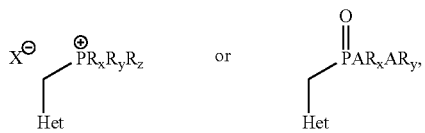

where A can be a bond or O and wherein $R_x$, $R_y$, and $R_z$ are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl and X is an anion, preferably halogen or $RCOO^-$ anion, more preferably chloro, bromo or trifluoroacetate;

and Het is selected so that it forms a heterocyclic skeleton of a statin, and is preferably selected from:

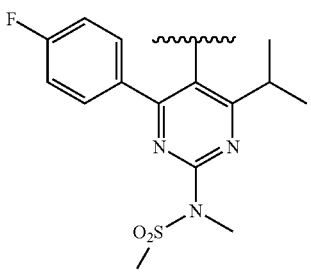

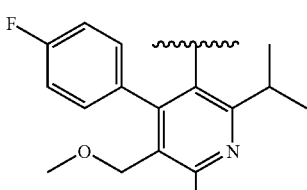

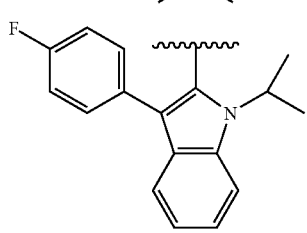

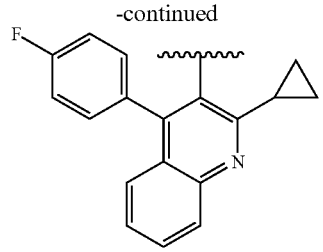

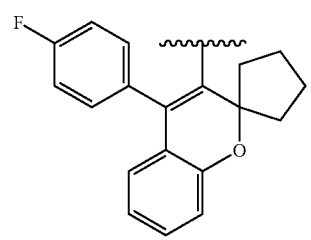

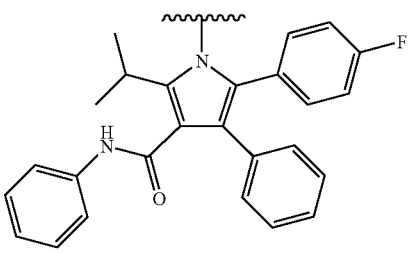

whereupon after the workup, which comprises removal of the protecting group and optional hydrolysis of the lactone and conversion into free acid or salt thereof, and may comprise before hydrolysis (if needed) introduction of hydrogen atoms to a double bond, the rosuvastatin, cerivastatin, fluvastatin, pitavastatin, bervastatin, atorvastatin or their analogs or salt thereof are formed.

The intermediate compound IX is the same regardless of which statin is being prepared. It is peculiar that this compound may exist in two tautomeric forms:

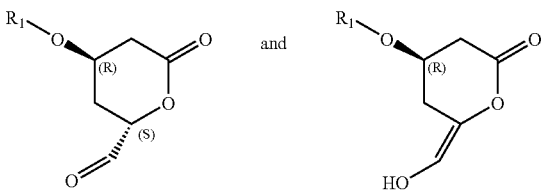

of which the latter does not undergo Wittig reaction, thus diminishing yield and/or increasing side products. In non-polar solvents in equilibrium, we can observe only one form of IX which corresponds to an aldehyde. The forms may be observed in different solvent systems using $^{13}C$ NMR by carefully examining spectra between 150 and 110 ppm for olefine signals. Moreover, only the keto form is present after conditioning (letting it dissolve for up to 1 week) of the solid IX in toluene, chloroform or dichloromethane or hexane, preferably toluene, which is therefore also preferred and advantageous solvent for Wittig reaction.

Moreover, the compound IX is also prone to hydration into its hydrate,

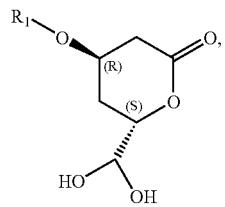

which is also not suitable for Wittig reaction. We have studied the aldehyde-hydrate equilibrium in order to increase the yield of Wittig reaction. Studying this reaction we discovered that toluene is a solvent which significantly increases the yield compared to THF, where equilibrium forms at around half of the compound as aldehyde and half as hydrate, thus THF, which is commonly used as the solvent for Wittig reaction, is not suitable, and we have discovered that in chlorinated solvents such as (chloroform, dichloromethane) hexane and preferably toluene the equilibrium is shifted towards aldehyde.

The invention provides a simple process for preparation of an intermediate IX from IVa, which is in turn prepared in only 5 steps from commercially available (S)-ethyl-3-hydroxy-4-chlorobutyrate. Specifically (4R,6S)-4-(tert-butyldimethylsilyloxy)-6-(iodomethyl)-tetrahydropyran-2-one (6a) with an overall yield of 23-31% of the desired stereoisomer, which is considerably higher than the known methods.

The intermediate compound IX used in the process of our invention is prepared from compound VIa (4R,6S)-4-(protected hydroxy)-6-(halomethyl)-tetrahydropyran-2-one or its derivative (X"=alkylsulfonyl or arylsulfonyl) by converting via compound of Formula VII (an ester such as pivaloate, chloroacetate, dichloroacetate, trichloroacetate, trifluoroacetate, methoxyacetate, triphenylmethoxyacetate, phenoxyacetate and its derivatives, phenylacetate and its derivatives, diphenylacetate, 3-phenylpropionate, pentenoate, 4-oxopentanoate, pentenoate, preferably acetate) into compound of Formula VIII, and oxidizing into compound of Formula IX.

This conversion into compound VII, where $R_4$ is an optionally substituted alkyl is necessary because the attempted direct conversion of halo derivative into hydroxyl derivative either yielded only degradation products or caused the opening of lactone ring.

The needed stereochemistry is achieved in the last step of synthesis of intermediate compound VI, which is prepared by halogen-mediated cyclization of compound V using molecular halogens such as iodine, bromine or chlorine as a source of halogen electrophiles. Alternative sources of halogens can also be applied for this reaction. Most commonly used are alkali or earth alkali halides or oxohalides such as KI, $KI_3$, $Ca(OCl)_2$, interhalogens such as iodine monochloride (I—Cl), iodine monobromide (I—Br) which have higher reactivity than elemental iodine and halogen(I) reagents such as iodonium acetate (I—OAc), N-iodosuccinimide (NIS), N-bromosuccinimide (NBS), bispyridine iodonium tetrafluoroborate ($PY_2IBF_4$). Hypervalent halogen electrophiles such as diacetoxy iodobenzene, bis(trifluoroacetoxy)iodobenzene, hydroxy(tosyloxy)iodobenzene (Koser's reagent) are also applicable for halocyclization reaction. However, molecular iodine is preferably used for conversion of V into mixture of (R,S) and (R,R)-diastereoisomers of lactone VIa and VIb. Conveniently the reaction is performed in such matter that (R,S)-diastereoisomer is formed in excess of (R,R)-diastereoisomer and if desired the (R,S)-diastereoisomer is separated from the mixture giving optically pure compound VIa. X" can be further substituted so that X" is thus a suitable substituent, preferably halo, cyano, alkylsulfonyl or arylsulfonyl, most preferably iodo.

Compound V can be prepared from compound of formula III by reaction with an appropriate Grignard reagent (vinyl magnesium halide)

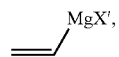

where X' is a halogen, preferably chloride preferably in the presence of orthophosphite derivative and copper(I) halide, giving compound of formula IV which is hydrolyzed into compound of Formula V.

A suitable starting compound for an overall synthesis is an alkyl 3(S)-hydroxy-4-chlorobutyrate I wherein $R_2$ is preferably $C_1$-$C_8$ alkyl or $C_5$-$C_7$ cycloalkyl which may be optionally substituted, preferably by an alkyl or aryl, alternatively a starting compound may be a derivative of I, wherein for example —$COOR_2$ may also be an amide of formula —$CONR_aR_b$, where $R_a$ and $R_b$ may independently be H, an optionally substituted $C_1$-$C_8$ alkyl or $C_5$-$C_7$ cycloalkyl, aryl or can together with N form a heterocycle. Substituted in this specification means that the substituted moiety bears one or more substituents, which are preferably selected from acyl, alkyl, alkenyl, cycloalkyl, cycloalkenyl, aryl, heteroaryl, halo, nitro, amino, alkoxy. Unless otherwise stated alkyl and aryl in this specification will preferably mean alkyl having up to 12 carbon atoms, preferably having 1, 2, 3, 4, 5, 6 or 7 carbon atoms and aryl having up to 3 condensated aromatic rings, which may contain one or more heteroatoms, more preferably a phenyl which may be additionally substituted.

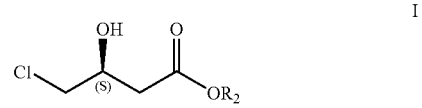

However any halo derivative or similar compound may be used. It is preferred to use iodo derivative or that said compound is converted to its iodo derivative of Formula II, where X is I and $R_2$ as defined above.

In subsequent step, OH group of compound of Formula II is protected by any suitable protecting agent giving compound of Formula III where $R_1$ is suitable protecting group, preferably silyl, more preferably $C_1$-$C_8$ trialkylsilyl, $C_1$-$C_8$ dialkylarylsilyl, $C_1$-$C_8$ alkyldiarylsilyl, where alkyls may be same or different, preferably aryl is phenyl and alkyls have 1 to 4 C atoms.

The process as described above provides statins selected from the group comprising rosuvastatin, cerivastatin, fluvastatin, pitavastatin, bervastatin, atorvastatin or analogs thereof which may be incorporated into pharmaceutical composition. Those statins are advantageous to those produced in alternative processes where the separation of stereoisomers is achieved in later stages. It is known that stereoisomers are hard to remove; however, purification processes following the early separation of compounds VIa and VIb still provide a chance to remove part of the undesired stereoisomers. Thus the patients being administered said compositions will achieve lower loading of undesired stereoisomers which causes reduced level of side effects.

In one embodiment of the invention a compound (4R,6S)-4-(tert-butyldimethylsilyloxy)-6-(iodomethyl)-tetrahydropyran-2-one (6a) corresponding to general formula VIa where $R_1$ is tert-butyldimethylsilyl is prepared and converted into suitable precursor for a statin. For example (6a) may be converted to (2S,4R)-4-(tert-butyldimethylsilyloxy)-6-oxo-tetrahydro-2H-pyran-2-carbaldehyde (9) corresponding to general formula IX where $R_1$ is tert-butyldimethylsilyl, which can be further coupled to an appropriate heterocyclic system, in the specific embodiment pyrimidine system, whereupon after the removal of protecting group and lactone ring opening and conversion into salt, in the specific embodiment rosuvastatin is formed.

One way to prepare (6a) is known from *J. Chem. Soc., Perkin Trans.* 1, 1991, 133-140 starting from methyl 2-cyanoacetate. Chloro analogue (compound of formula VIa where X" is Cl) can be made enzymatically. 3(R)-(tert-butyldimethylsilyloxy)-5-hexenoate (4), as described in *J. Antibiot.* 2002, 55, 147-154, can be converted to (R)-3-(tert-butyldimethylsilyloxy)-5-hexenoic acid (5) according to *Tetrahedron Lett.* (43) 2002, 4381-4384.

In the first synthetic step, (S)-ethyl 3-hydroxy-4-iodobutyrate (2) is prepared from ethyl 3(S)-hydroxy-chlorobutyrate (1) by reaction with NaI. Suitable solvents are selected from amides, preferably selected from N,N-dimethylformamide (DMF), N,N-dimethylacetamide (DMA), hexamethylphosphortriamide (HMPTA); N-methylpyrrolidone (NMP); N,N'-dimethylpropyleneurea (DMPU); N,N,N',N'-tetramethylurea (TMU); dimethylsulfoxide (DMSO); acetonitrile; lower alcohols; ketones, preferably acetone. The reaction can be performed at temperatures between 58° C. to 90° C. Preferably at 60° C., and is accomplished in a period from half a day up to more days, preferably in 41 hours (at 90° C.) to 120 hours (at 60° C.).

In second step, a protecting group is introduced, thus (S)-ethyl 3-(tert-butyldimethylsilyloxy)-4-iodobutyrate (3) is prepared from ethyl 3(S)-hydroxy-4-iodobutyrate and tert-butyl(chloro)dimethylsilane (TBSCl). The molar amount of later may be less than 1.5 mol per mol of butyrate. The reaction is conveniently done in the presence of a base, selected from amines, imidazoles and pyridines, preferably imidazole in solvents such as amides (DMF, DMA, HMPTA, NMP, DMPU, TMU), DMSO, nitriles (acetonitrile), chlorinated hydrocarbons (dichloromethane, chloroform), aromatic hydrocarbons (toluene), preferably in DMF. The reaction can be performed at temperatures between 0° C. to 10° C. and it is preferably performed in the presence of NaI, preferably at 0° C. The reaction is accomplished in a period from one hour up to a day, preferably in 12 to 17 hours.

In the third step, ethyl 3(R)-(tert-butyldimethylsilyloxy)-5-hexenoate (4) is prepared from vinylmagnesium halide and (S)-ethyl 3-(tert-butyldimethylsilyloxy)-4-iodobutyrate, solvents such as amides (DMF, DMA, HMPTA, NMP, DMPU, TMU) or DMSO are used, preferably N,N'-dimethylpropyleneurea (DMPU) preferably in presence of copper halide, preferably CuI and orthophosphite derivative with formula,

where each of R', R", and R'" are same or different $C_1$-$C_4$ alkyl, $C_5$-$C_7$ cycloalkyl, or aryl which may be optionally substituted, preferably $C_1$-$C_4$ alkyl, phenyl, benzyl, most preferably P(OEt)$_3$. The reaction can be performed at temperatures between −45° C. to −25° C., preferably at −40° C. The reaction can be performed with vinylmagnesium chloride, bromide or iodide, preferably with vinylmagnesium chloride. The reaction is accomplished within up to a day, preferably within 3 hours to 5 hours whereupon it is quenched by addition of saturated aqueous NH$_4$Cl solution at −10° C. to 0° C. The crude product is extracted with a water-immiscible solvent, and the organic solution is washed with diluted acids such as H$_2$SO$_4$, HCl, H$_3$PO$_4$ etc.

In each of those three steps, the products are conveniently isolated by extraction with water-immiscible solvents like ethers such as Et$_2$O (diethyl ether), i-Pr$_2$O (diisopropyl ether), t-BuMeO (tert-butylmethyl ether) or alkanes such as pentane, hexane, heptane or chlorinated hydrocarbons such as methylene chloride, preferably with t-BuMeO. Product can be purified by vacuum distillation at suitable temperature (i.e., 70-90° C. for first step, 70-95° C. for second step, and 55-80° C. for third step) and 0.100-0.500 mbar.

In fourth step until now not yet isolated compound (R)-3-(tert-butyldimethylsilyloxy)-5-hexenoic acid (5) is prepared by hydrolysis of ethyl 3(R)-(tert-butyldimethylsilyloxy)-5-hexenoate with an alkali in a solvent such as MeOH. The reaction can be performed at temperatures between 0° C. to 80° C., preferably at 40° C. The reaction can be performed in alcohols, THF, amide solvents or a mixture of these solvents with water, but preferably in alcohols. The reaction is accomplished in a matter of minutes or hours, preferably in 0.5 hours to 3 hours. The hydrolysis of the ester can be performed with NaOH, KOH, LiOH, CsOH, Ca(OH)$_2$ or Ba(OH)$_2$ as a base, preferably with KOH. Following the hydrolysis acidification to pH 2 can be performed with diluted acids such as HCl, H$_2$SO$_4$, H$_3$PO$_4$etc., preferably with HCl. Again extraction with ethers and alkanes as described above, preferably with t-BuMeO, is a feasible isolation method.

In the fifth step, the (R)-3-(tert-butyldimethylsilyloxy)-5-hexenoic acid (5) is converted by iodine to a mixture of (4R,6S)-4-(tert-butyldimethylsilyloxy)-6-(iodomethyl)-tetrahydropyran-2-one and (4R,6R)-4-(tert-butyldimethylsilyloxy)-6-(iodomethyl)-tetrahydropyran-2-one (6a and 6b) as pale yellow solid. This solid is recrystallized preferably several times from n-pentane to afford (4R,6S)-4-(tert-butyldimethylsilyloxy)-6-(iodomethyl)-tetrahydropyran-2-one (d.e. 99.3%) (6a) as colourless needles in 43% yield. This simple step introduces the needed chirality into molecules. The reaction can be performed at temperatures between −10° C. to 10° C., preferably at 0° C. Again extraction with ethers and alkanes as above, preferably with t-BuMeO may be used. The optically pure compound (4R,6S)-4-(tert-butyldimethylsilyloxy)-6-(iodomethyl)-tetrahydropyran-2-one can be isolated by industrial scale HPLC.

Diastereoisomers (in particular embodiment starting with the ratio 6a:6b=4:1) can be separated at room temperature on normal phase silica column (PHENOMENEX 4.6×150 mm, $d_p$=5 µm) using different compositions of hexane and t-BuMeO as a mobile phase.

Optically pure compound will mean diastereoisomeric excess (d.e.) above 96%, preferably above 99%, more preferably above 99.7% (d.e. 99% will mean 99.5%/0.5% ratio) as determined by HPLC.

The optically pure compound (4R,6S)-4-(tert-butyldimethylsilyloxy)-6-(iodomethyl)-tetrahydropyran-2-one is also alternatively prepared from (4R,6S)-4-(tert-butyldimethylsilyloxy)-6-(chloromethyl)-tetrahydropyran-2-one (VIa, X"=Cl) which can be obtained from unprotected (4R,6S)-6-(chloromethyl)-4-hydroxy-tetrahydropyran-2-one. (4R,6S)-

6-(chloromethyl)-4-hydroxy-tetrahydropyran-2-one can be prepared enzymatically by one-pot tandem aldol reaction catalyzed by a deoxyribose-5-phosphate aldolase (DERA) followed by chemical oxidation step as described in *Proc. Natl. Acad. Sci. USA* 2004, 101, 5788-5793. Analogous procedure can be applied if $R_1$ is a protecting group different from exemplified tert-butyldimethylsilyl.

In sixth reaction step, (2S,4R)-4-(tert-butyldimethylsilyloxy)-6-oxo-tetrahydro-2H-pyran-2-yl)methyl acetate (7) is prepared from (4R,6S)-4-(tert-butyldimethylsilyloxy)-6-(iodomethyl)-tetrahydropyran-2-one. The reaction can be performed at temperatures between 0° C. to 130° C., preferably at 120° C. The reaction can be performed in amide solvents selected from N,N-dimethylformamide (DMF), N,N-dimethylacetamide (DMA), N-methylpyrrolidone (NMP), N,N'-dimethylpropyleneurea (DMPU) or hexamethylphosphortriamide (HMPA); dimethylsulfoxide (DMSO) or acetic acid (AcOH), preferably in AcOH. The reaction is accomplished in up to one day, preferably in 1 hour to 17 hours. The acylation (iodine substitution) can be performed with an acylating reagent selected from the group consisting of NaOAc, KOAc, LiOAc, CsOAc, AgOAc, CuOAc, Ca(OAc)$_2$, Mg(OAc)$_2$ or R$_4$NOAc as a nucleophilic reagent, preferably with LiOAc or AgOAc. Isolation of the crude product with extraction can be performed with AcOEt, ethers and alkanes as above, preferably with t-BuMeO.

In seventh reaction step, (2S,4R)-4-(tert-butyldimethylsilyloxy)-6-oxo-tetrahydro-2H-pyran-2-yl)methyl acetate (7) is deacylated to (4R,6S)-4-(tert-butyldimethylsilyloxy)-6-(hydroxymethyl)-tetrahydropyran-2-one (8). Reaction may proceed with alkali hydroxides, but the most selective reagent is preferred. Deacylation can be performed also with enzymes such as Porcine Pancreatic Lipase, Lipase MY, Lipase PS, Lipase Al, Candida Lipase and Alcalase, or reagents selected from group consisting of guanidine and guanidine/guanidinium nitrate, HBF$_4$×Et$_2$O/MeOH and BF$_3$×Et$_2$O/MeCN, DBU/MeOH, hydrazine/MeOH and hydrazine hydrate/THF, cyanide/MeOH, I$_2$/MeOH or tin catalysts like dialkylchlorostanyl hydroxide dimers such as [t-Bu$_2$SnOH(Cl)]$_2$. Dialkylchlorostanyl hydroxide dimers are preferred and [t-Bu$_2$SnOH(Cl)]$_2$ is most preferred. The reaction using [t-Bu$_2$SnOH(Cl)]$_2$ can be performed at temperatures between 0° C. to 40° C., preferably at 25° C. The reaction can be performed in alcohols such as MeOH, EtOH, i-PrOH or in mixtures of these alcohols with ethers such as: THF, Et$_2$O, i-Pr$_2$O, t-BuMeO. The 5-15 mol % of tin catalyst can be used for the deacetylation reaction. The reaction is accomplished in up to one day, preferably 4-17 hours. Isolation of the product can be performed with crystallization. For this purpose alkanes or ethers as above, preferably hexane, may be used.

In eighth reaction step (2S,4R)-4-(tert-butyldimethylsilyloxy)-6-oxo-tetrahydro-2H-pyran-2-carbaldehyde (9) is formed from (4R,6S)-4-(tert-butyldimethylsilyloxy)-6-(hydroxymethyl)-tetrahydropyran-2-one (8) by a suitable oxidation such as dimethylsulfoxide-mediated oxidations (Swern oxidation: DMSO-(COCl)$_2$ couple, Pfitzner-Moffatt procedure: DMSO-dicyclohexylcarbodiimide (DCC) couple, Parikh-Doering procedure: DMSO-SO$_3$×Py couple), N-oxoammonium-mediated oxidations (2,2,6,6-tetramethyl-1-piperidinyloxyl (TEMPO)-oxidant couple), oxidations with organic hypervalent iodine compound such as Dess-Martin periodinane (DMP) or o-iodoxybenzoic acid (IBX or SIBX), oxidations with chromium (VI) oxidants such as Collins reagent (CrO$_3$×Py$_2$), pyridinum dichromate (PDC) (couple PDC-activated molecular sieves 4 Å), pyridinum chlorochromate (PCC), oxidations with manganese derivatives such as MnO$_2$ and BaMnO$_4$ or oxidations with tetra-n-propylammonium perruthenate: Pr$_4$N$^+$RuO$_4^-$ (TPAP). The reactions can be performed at temperatures between 0 to 40° C. (Dess-Martin periodinane and couple PDC-activated molecular sieves 4 Å) and −80° C. to −40° C. (Swern). The reaction can be performed in CHCl$_3$, CH$_2$Cl$_2$, ionic liquid (IL) like 1-butyl-3-methylimidazolium tetrafluoroborate (BMIMBF$_4$) or DMSO. The reaction is accomplished in 1-24 hours. Isolation of the crude product with extraction can be preformed with AcOEt, ethers or alkanes as above. Preferably with PhMe, MTBE or AcOEt.

The analogous reaction conditions may be applied also to processes within the scope of this invention where $R_1$ is different than herein used t-butyldimethylsilyl and $R_2$ is different than herein used Et. The reaction times of herein described reactions may thus be modified and in general depend on reaction conditions, especially temperature, solvents used and presence of any catalysts.

The formed compound of general formula IX may be used to synthesize statins. The subsequent reaction steps will differ depending on which final compound is synthesized.

Wittig coupling of compound of formula IX is performed in the presence of a strong base, preferably metal amide or silazane, most preferably selected from sodium hexametydisilazane, potassium hexametydisilazane, lithium hexametydisilazane, lithium diisopropylamide, sodium hydride, butyllithium or Grignard reagents at temperatures between −80° C. and 40° C. in an organic solvent or a mixture of organic solvents, preferably in toluene or a mixture of another organic solvent and toluene or tetrahydrofuran and a process may further comprise a treatment of the reaction mixture, comprising steps: (optionally) concentrating a reaction mixture; acidifying a reaction mixture in the presence of water and extracting a product into water immiscible organic solvent; (optionally) washing an organic solvent solution of a product with water, water solution of an alkali salt or ammonium salt, and/or water solution of mineral acid; (optionally) washing an organic solvent solution of a product with a mixture water/polar aprotic organic solvent; (optionally) drying a solution with a drying agent; concentrating a solution to obtain residue, preferably by evaporation; and purifying a residue by column chromatography on silica.

In the specific embodiment related to rosuvastatin in the subsequent reaction step, (2S,4R)-4-(tert-butyldimethylsilyloxy)-6-oxo-tetrahydro-2H-pyran-2-carbaldehyde (9) is reacted under condition of Wittig coupling (in the presence of base) with a ((4-(4-fluorophenyl)-6-isopropyl-2-(N-methylmethylsulfonamido)pyrimidin-5-yl)methyl)triphenylphosphonium halide or any other ((4-(4-fluorophenyl)-6-isopropyl-2-(N-methylmethylsulfonamido)pyrimidin-5-yl) methyl)phosphonium salt or alternatively di-1-propyl({4-(4-fluorophenyl)-6-isopropyl-2-[methyl(methylsulfonyl) amino]-5-pyrimidinyl}methylphosphonate or any other ({4-(4-fluorophenyl)-6-isopropyl-2-[methyl(methylsulfonyl) amino]-5-pyrimidinyl}methylphosphonate ester to give N-(5-((E)-2-((2S,4R)-4-(tert-butyldimethylsilyloxy)-6-oxo-tetrahydro-2H-pyran-2-yl)vinyl)-4-(4-fluorophenyl)-6-isopropylpyrimidin-2-yl)-N-methylmethanesulfonamide (10). As a base lithium hexamethyldisilazane (LiHMDS), potassium hexamethyldisilazane (KHMDS), sodium hexamethyldisilazane (NaHMDS), lithium diisopropylamide (LDA), sodium hydride, butyllithium or Grignard reagents, preferably sodium hexamethyldisilazane may be used and the reaction can be performed in ethers selected from THF, Et$_2$O, i-Pr$_2$O, t-BuMeO; alkanes selected from pentane, hexane, heptane, toluene or in mixtures of these solvents. The preferred solvents are anhydrous toluene and tetrahydrofuran.

The reaction can be performed at temperatures between −80° C. to 40° C., preferably at 0 to 30° C. The reaction is accomplished in 1-2 hours. Isolation of the crude product with extraction can be performed with AcOEt, ethers or alkanes as above. preferably with t-BuMeO.

The silyl protecting group may be removed and lactone opened to produce a rosuvastatin free acid or its salt, optionally an amine, which may be converted to hemicalcium salt.

The deprotection can be performed at temperatures between 0° C. to 80° C., preferably at 25 or 60° C. in suitable solvent, preferably a solvent selected from alcohols, THF, acetonitrile, methyltetrahydrofuran, dioxane, $CH_2Cl_2$, and more preferably in alcohols and THF. The usual deprotecting reagents may be used such as ammonium fluoride, $FeCl_3$, TMSCl/HF.2$H_2O$, chloroethylchloroformate (CEC), $Ph_3PCH_2COMeBr$. Opening of lactone takes place in preferably a 4:1 to 2:1 mixture of THF/$H_2O$ as well as a pure THF at temperatures between 20° C. to 60° C. with suitable alkali such as NaOH, KOH, ammonia or amines. The hydrolysis is accomplished in 30 minutes (at 60° C.) to 2 hours (at 20° C.). After that, evaporation of solvents under reduced pressure can be conducted at temperatures between 10° C. to 50° C. and conversion to calcium salt, preferably by addition of Ca(OAc)$_2 \times H_2O$ can be performed at temperatures between 0° C. to 40° C. which can be added in one portion or dropwise in 5 to 60 minutes. After the addition of Ca(OAc)$_2 \times H_2O$ suspension can be stirred at temperatures between 0° C. to 40° C. from 30 minutes to 2 hours.

To produce other statins the (2S,4R)-4-(tert-butyldimethylsilyloxy)-6-oxo-tetrahydro-2H-pyran-2-carbaldehyde (9) is reacted under analogous condition of Wittig coupling with an appropriate reagent followed by hydrogenation when needed.

Statin-containing nitrogen, such as atorvastatin, can be prepared in an analogous manner by using a compound of formula VIa wherein X″ is cyano by conversion into an amine and cyclization with an appropriate derivative to give an intermediate, which can be upon workup converted into said statin-containing nitrogen. Thus (6a) may be converted in the presence of a cyanide to 2-((2R,4R)-4-(tert-butyldimethylsilyloxy)-6-oxo-tetrahydro-2H-pyran-2-yl)acetonitrile followed by reduction of the cyano group and subsequent cyclization condensation of the amino group with appropriate precursor to afford the statin-containing nitrogen, preferably atorvastatin derivative.

Summary of the aspects of the invention is as follows:
The first main aspect of our invention is process for preparing the compound of formula VIa

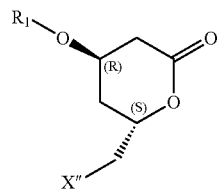

wherein X″ is halo, preferably iodo; and $R_1$ is a protecting group, preferably silyl or benzyl, [more preferably selected from optionally substituted $C_1$-$C_8$ trialkylsilyl, $C_1$-$C_8$ dialkylarylsilyl, $C_1$-$C_8$ alkyldiarylsilyl, where alkyls may be same or different], comprising steps:
(optionally) reacting alkyl 3(S)-hydroxy-4-chlorobutyrate of formula I,

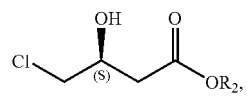

wherein $R_2$ is an optionally substituted $C_1$-$C_8$ alkyl or $C_5$-$C_7$ cycloalkyl, or, alternatively —COOR$_2$ may also form an amide of formula —CONR$_a$R$_b$, where R$_a$ and R$_b$ may independently be H, an optionally substituted $C_1$-$C_8$ alkyl or $C_5$-$C_7$ cycloalkyl, aryl or can together with N form a heterocycle with an iodide to give a alkyl 3(S)-hydroxy-4-iodobutyrate of formula II

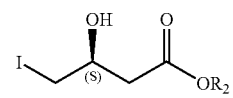

wherein $R_2$ is as above;
protecting the compound of Formula II to give a protected derivative of formula III,

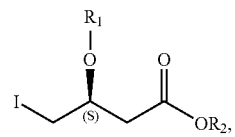

wherein $R_1$ and $R_2$ are as above;
reacting the compound of formula III with vinylmagnesium halide
[preferably vinyl magnesium chloride] in presence of copper(I) halide and phosphite derivative with formula:

where each of R′, R″, and R‴ are same or different $C_1$-$C_4$ alkyl, $C_5$-$C_7$ cycloalkyl, or aryl which may be optionally substituted
to give an alkene of formula IV,

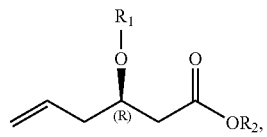

wherein $R_1$ and $R_2$ are as above
hydrolyzing [preferably with an alkali followed by acidification] the compound of formula IV to give compound of formula V

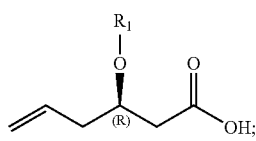

reacting compound of formula V, wherein $R_1$ is as above, with a source of halogen [preferably selected from the group consisting of iodine, bromine, chlorine, alkali metal and earth alkali metal halides or oxohalides, interhalogens, haloacetates, N-iodosuccinimide (NIS), N-bromosuccinimide (NBS), bispyridine iodonium tetrafluoroborate and hypervalent halogen electrophiles] in the presence of $NaHCO_3$; and (optionally) separating the mixture of diastereoisomers obtained in previous step.

In an aspect the compound of the Formula VIa is isolated in optical purity higher than 99% d.e. as determined by HPLC.

Another aspect of the invention is use of a solvent selected from the group consisting of t-BuMeO, i-$Pr_2O$, pentane, hexane, heptane, cyclopentane, cyclohexane, AcOEt, methylene chloride, chloroform and mixture(s) thereof in any of the processes as described above and use of vacuum distillation in the process of purification of the compounds obtained in any of the processes as claimed above.

Additionally to above described process to compound VI, a second main aspect of our invention further comprises preparing the compound of formula IX

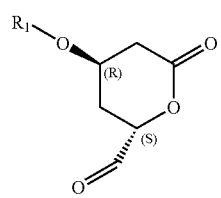

where $R_1$ is as defined above from compound of formula VIa

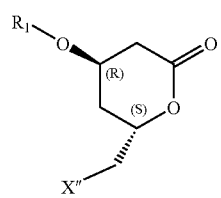

where X" is a halogen, alkylsulfonyl, or arylsulfonyl, and where those sulfonyl derivatives may be prepared from halo compounds by conventional methods.

More specifically in the just described process the compound of formula IX

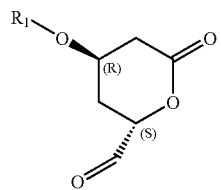

wherein $R_1$ is as defined above, is prepared by process comprising one or more steps selected from g) converting the compound of formula VIa

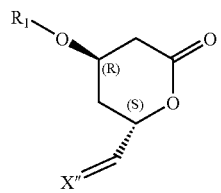

where X" is halo, alkylsulfonyl, or arylsulfonyl into compound of formula VII

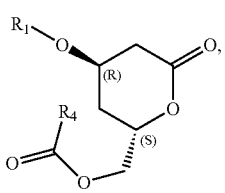

wherein $R_4$ is (optionally halo, alkyl, aryl, alkyl oxy or aryl oxy substituted) $C_1$-$C_4$ alkyl;

h) converting compound of formula VII in compound of formula VIII

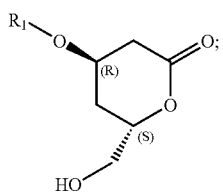

and i) converting the compound of formula VIII by oxidation into compound of formula IX,

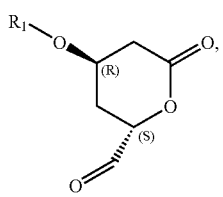

Specific aspects of respective steps are that g) is performed with an acylation reagent selected from the group consisting of NaOAc, LiOAc, KOAc, CsOAc, AgOAc, CuOAc, Mg(OAc)$_2$, Ca(OAc)$_2$, R$_4$NOAc; h) is performed by deacylation with an organotin compound selected from dibutyltin oxide or [t-Bu$_2$SnOH(Cl)]$_2$ or by a reaction with an enzyme selected from group consisting of Porcine Pancreatic Lipase, Lipase MY, Lipase PS, Lipase Al, Candida Lipase and Alcalase, or with a reagent selected from the group consisting of guanidine and guanidine/guanidinium nitrate, HBF$_4$×Et$_2$O/MeOH and BF$_3$×Et$_2$O/MeCN, DBU/MeOH, hydrazine/MeOH and hydrazine hydrate/THF, cyanide/MeOH, I$_2$/MeOH; i) is performed by an oxidation reaction selected from dimethylsulfoxide-mediated oxidations (Swern oxidation: DMSO-(COCl)$_2$ couple, Pfitzner-Moffatt procedure: DMSO-dicyclohexylcarbodiimide (DCC) couple, Parikh-Doering procedure: DMSO-SO$_3$×Py couple), N-oxoammonium-mediated oxidations (2,2,6,6-tetramethyl-1-piperidinyloxyl (TEMPO)-oxidant couple, oxidations with organic hypervalent iodine compound selected from Dess-Martin periodinane (DMP) and o-iodoxybenzoic acid (IBX or SIBX), oxidations with chromium (VI) oxidants selected from Collins reagent (CrO$_3$×Py$_2$), pyridinum dichromate (PDC) (couple PDC-activated molecular sieves 4 Å), pyridinum chlorochromate (PCC), oxidations with manganese derivatives selected from MnO$_2$ and BaMnO$_4$ or oxidations with tetra-n-propylammonium perruthenate: Pr$_4$N$^+$ RuO$_4^-$ (TPAP).

Yet another aspect of the invention is a process for manufacturing a compound of formula XI:

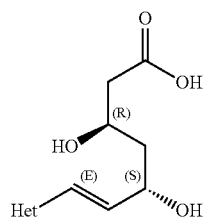

or a salt, amide, or lactone thereof,
wherein Het is selected from group consisting of:

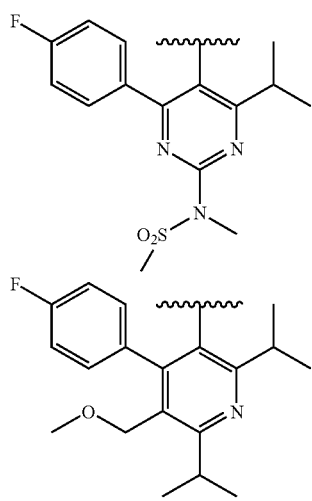

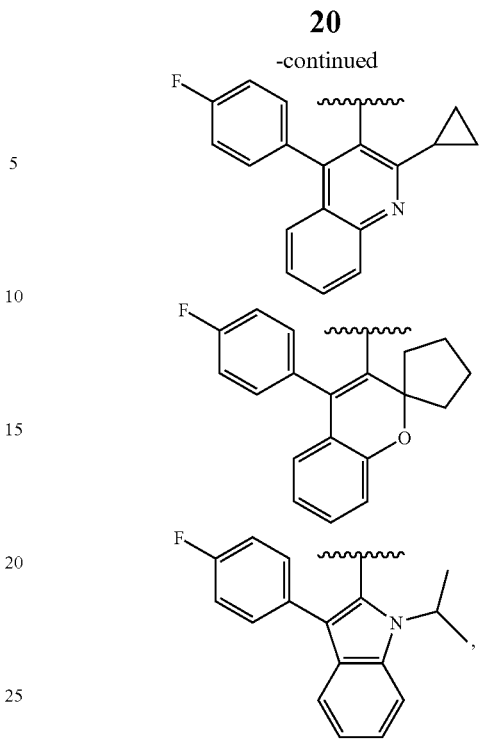

comprising:
preparing an intermediate of formula VIa

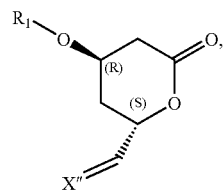

wherein R$_1$ and X" are as defined above,
by the process which is the first main aspect of the invention as described above
preparing the intermediate of formula IX

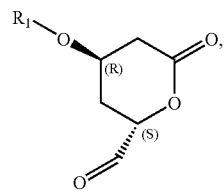

wherein R$_1$ is as defined above
from the intermediate of formula VIa by the process which is the second main aspect of this invention as described above; and reacting the intermediate of formula IX with the compound of formula

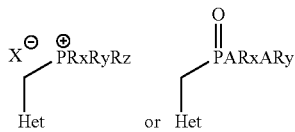

where A can be a bond or O, and wherein $R_x$, $R_y$, and $R_z$, are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl, $X^-$ is anion [preferably halide or alkanoate]

and Het is as defined above, and optionally comprising one or more subsequent steps in which the compound of formula X

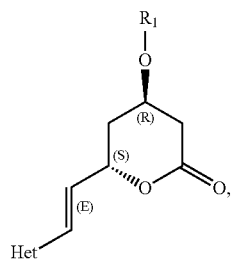

wherein $R_1$ and Het are as defined above, is transformed into a compound of formula XI

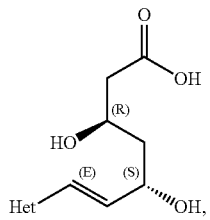

wherein $R_1$ and Het are as defined above, or a salt, amide, or lactone thereof. Preferably Het is a heterocyclic skeleton of rosuvastatin with formula

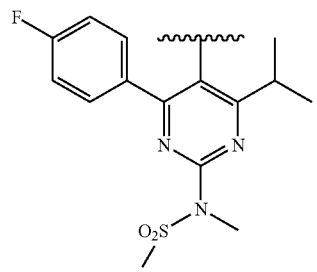

Another specific aspect of the invention is a process for manufacturing rosuvastatin, characterized in that it comprises steps:

(optionally) reacting alkyl 3(S)-hydroxy-4-chlorobutyrate of formula I,

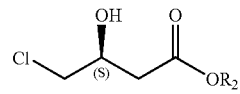

wherein $R_2$ is an optionally substituted $C_1$-$C_8$ alkyl or $C_5$-$C_7$ cycloalkyl, or, alternatively —$COOR_2$ may also form an amide of formula —$CONR_aR_b$, where $R_a$ and $R_b$ may independently be H, an optionally substituted $C_1$-$C_8$ alkyl or $C_5$-$C_7$ cycloalkyl, aryl or can together with N form a heterocycle with an iodide to give a alkyl 3(S)-hydroxy-4-iodobutyrate of formula II

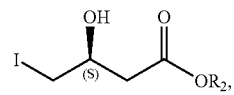

wherein $R_2$ is as above;

(optionally) protecting the compound of formula II to give a protected derivative of formula III,

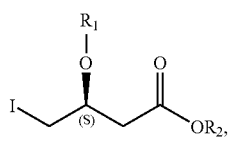

wherein $R_1$ and $R_2$ are as above;

reacting the compound of formula III with vinylmagnesium halide in presence of copper(I) halide and phosphite derivative with formula:

where each of R', R", and R'" are same or different $C_1$-$C_4$ alkyl, $C_5$-$C_7$ cycloalkyl, or aryl which may be optionally substituted to give an alkene of formula IV

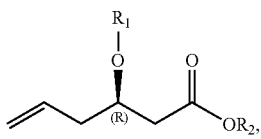

wherein $R_1$ and $R_2$ are as above;
hydrolyzing the compound of formula IV to give compound of formula V

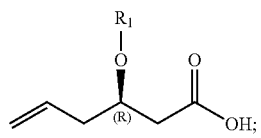

reacting compound of formula V, wherein $R_1$ is as above, with a source of halogen in the presence of $NaHCO_3$ to give compound of formula VI;
(optionally) separating the mixture of diastereoisomers obtained in previous step to obtain compound of formula VIa

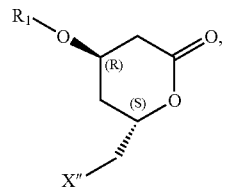

wherein X" is halo and $R_1$ as above;
converting the compound of formula VIa into compound of formula VIII,

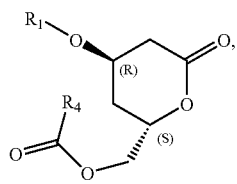

wherein $R_1$ is as above and $R_4$ is selected from (optionally halo or alkoxy or aryloxy substituted) $C_1$-$C_4$ alkyl
converting compound of formula VII in compound of formula VIII

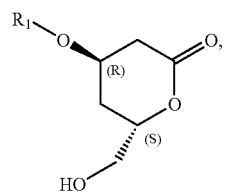

wherein $R_1$ is as above;
converting the compound of formula VIII by oxidation into compound of formula IX,

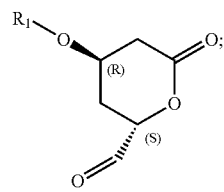

wherein $R_1$ is as above;
reacting said compound of formula IX with the compound of formula

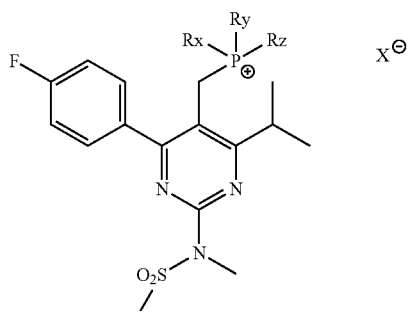

wherein $R_x$, $R_y$, and $R_z$, are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl, $X^-$ is anion [preferably halide or alkanoate] and removing the protecting group $R_1$; optionally purifying and converting the obtained compound into calcium salt.

Another aspect of the invention is the use for the synthesis of statins of an intermediate IX

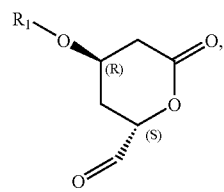

characterized in that it has been prepared from intermediate of formula VIa

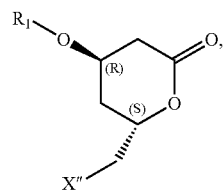

wherein X" is halo, arylsulfonyl or alkylsulfonyl and $R_1$ is a protecting group and also use for the synthesis of statins of an intermediate of formula

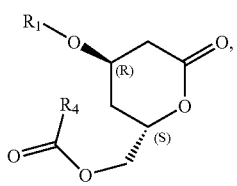

wherein $R_1$ is an optionally substituted $C_1$-$C_8$ trialkylsilyl, $C_1$-$C_8$ dialkylarylsilyl, $C_1$-$C_8$ alkyldiarylsilyl, where alkyls may be same or different and $R_4$ is (optionally halo, alkyl, aryl, alkyl oxy or aryl oxy substituted) $C_1$-$C_4$ alkyl.

New compounds of formula:

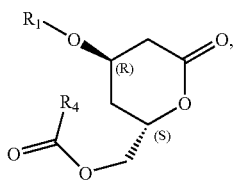

wherein $R_1$ is an optionally substituted $C_1$-$C_8$ trialkylsilyl, $C_1$-$C_8$ dialkylarylsilyl, $C_1$-$C_8$ alkyldiarylsilyl, where alkyls and aryls may be the same or different and $R_4$ is (optionally halo, alkyl, aryl, alkyl oxy or aryl oxy substituted) $C_1$-$C_4$ alkyl are also aspects of the invention as well as their use as intermediates in the synthesis of statins, preferably rosuvastatin, where preferably $R_4$ is $CH_3$, $C(CH_3)_3$, $CH_2Cl$, $CHCl_2$, $CCl_3$, $CF_3$, $CH_2OCH_3$, $CH_2OCPh_3$, $CH_2OPh$, $CH_2Ph$, $CHPh_2$, $CH_2CH_2Ph$, $CH=CHCH_2CH_3$ and $CH_2CH_2(C=O)CH_3$, and more preferably $R_1$ is t-butyldimethylsilyl and $R_4$ is $CH_3$.

Also an aspect of the invention are compounds of formula [and its use for the synthesis of statins, preferably rosuvastatin]

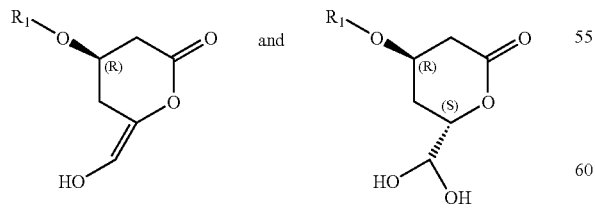

wherein $R_1$ is an optionally substituted $C_1$-$C_8$ trialkylsilyl, $C_1$-$C_8$ dialkylarylsilyl, $C_1$-$C_8$ alkyldiarylsilyl, where alkyls and aryls may be the same or different, preferably wherein $R_1$ is t-butyldimethylsilyl.

Related to that is also a process for converting compound of formula

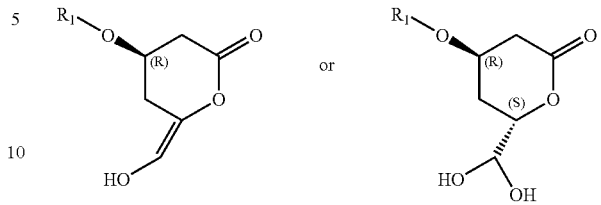

into compound of formula

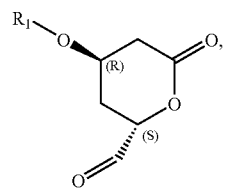

characterized by dissolving in chloroform, dichloromethane, hexane or toluene, preferably toluene, preferably for more than 24 h, more preferably more than 150 h.

The more specific aspect of the invention is a process for the manufacturing of a compound of the formula X

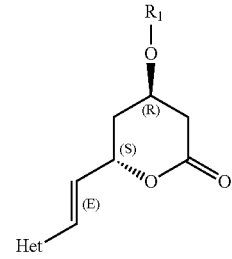

comprising Wittig reaction in which the compound of formula IX

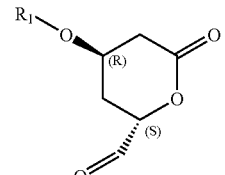

is reacted with a compound of formula

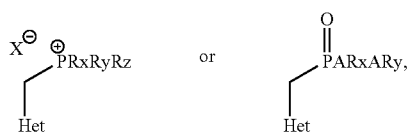

where A can be a bond or O and wherein $R_x$, $R_y$, and $R_z$, are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl, $R_1$ is a protecting group, X is an anion, and Het is selected so that it forms a heterocyclic skeleton of a statin, characterized in that the reaction is performed in solvent selected from the group consisting of, chloroform or dichloromethane, or hexane and preferably toluene.

Preferably Het is selected from group consisting of:

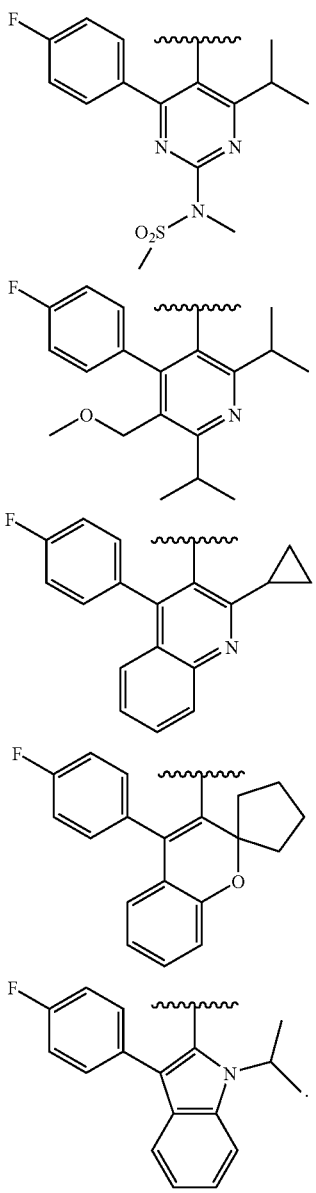

Another specific aspect of the invention is a process for the manufacturing of rosuvastatatin comprising Wittig reaction in which the compound of formula IX

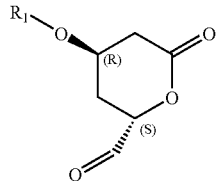

is reacted with a compound of formula

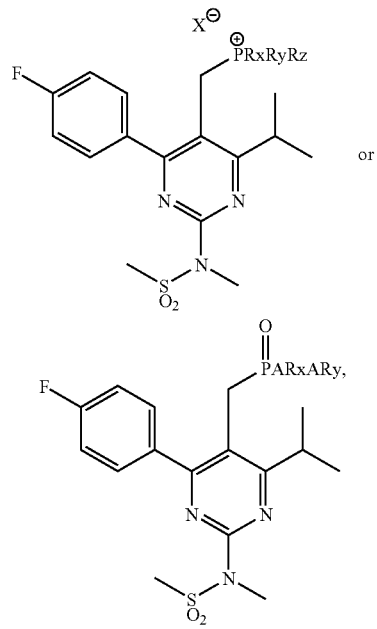

where A can be a bond or O and wherein $R_x$, $R_y$, and $R_z$, are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl, $R_1$ is a protecting group, X is an anion, and Het is selected so that it forms a heterocyclic skeleton of a statin, characterized in that the reaction is performed in toluene.

The Wittig reaction as described above is specifically characterized in that the compound of formula IX is dissolved in toluene at least 6 hours prior to reaction and/or that it is performed in the presence of a strong base at temperatures between −80° C. and 40° C., preferably from 0° C. to 40° C., more preferably from 10° C. to 35° C. Preferably a strong base is selected from the group of metal amides or silazanes, metal hydrides, lithium alkyls or lithium aryls, more preferably from lithium hexamethyldisilazane, sodium hexamethyldisilazane, potassium hexamethyldisilazane, lithium diisopropylamide, sodium hydride, butyllithium or Grignard reagents.

In an aspect of the invention, the process described above further comprises a treatment of the reaction mixture, comprising the following sequence of steps:

(optionally) concentrating a reaction mixture;

acidifying a reaction mixture in the presence of water and extracting a product into water-immiscible organic solvent;

(optionally) washing an organic solvent solution of a product with water, water solution of an alkali salt or ammonium salt, and/or water solution of mineral acid;
(optionally) washing an organic solvent solution of a product with a mixture of water/polar aprotic organic solvent;
(optionally) drying a solution with a drying agent;
concentrating a solution to obtain residue, preferably by evaporation; and
purifying a residue.

Specific aspect of the invention are the statins selected from the group comprising rosuvastatin, cerivastatin, fluvastatin, pitavastatin, bervastatin, atorvastatin or analogs thereof characterized in that it is manufactured by the process as described here and a pharmaceutical composition comprising a pharmaceutically acceptable carrier and a statin selected from rosuvastatin calcium, fluvastatin sodium, atorvastatin calcium manufactured by the process using the intermediate VIa

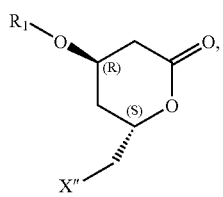

VIa wherein X" is halo and $R_1$ is a protecting group.

The various embodiments of the invention are presented in following examples,

EXAMPLE 1

Ethyl 3(S)-hydroxy-4-iodobutyrate (2)

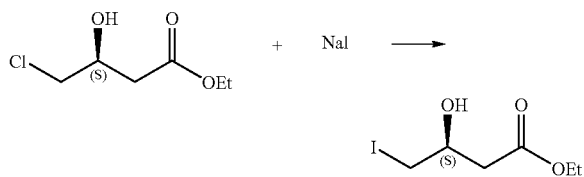

To a solution of ethyl 3(S)-hydroxy-chlorobutyrate (1) (639.0 g, 3.84 mol) in dry acetone (7.7 L) is added anhydrous NaI (2300 g, 15.34 mol). The mixture is stirred vigorously at 58-60° C. for 120 hours under argon atmosphere. The acetone is distilled off under the reduced pressure at 40-60° C. The residue is diluted with water (5.75 L) followed by the addition of saturated $Na_2S_2O_3$ solution (1.53 L) and t-BuMeO (2.3 L). The mixture is stirred vigorously at ambient temperature for 30 minutes. Then the organic layer is separated and the water phase is extracted additionally with t-BuMeO (2×1.15 L). The combined organic layers are washed with water (800 mL) and dried ($MgSO_4$). Evaporation of the solvent under the reduced pressure (20 mbar) at 40° C. affords 949.9 g (96%) of ethyl 3(S)-hydroxy-4-iodobutyrate (2) as yellow oil (GC purity 85.9%). A product with GC purity of 98-99% can be obtained by vacuum distillation (73-89° C. at 0.180-0.330 mbar) of the crude product. $^1$H NMR (300 MHz, $CDCl_3$): δ 4.17 (q, J=7.2 Hz, 2H), 3.99 (m, 1H), 3.34 (dd, J=10.3 and 5.2 Hz, 1H), 3.28 (dd, J=10.3 and 5.7 Hz, 1H), 3.21 (br s, 1H), 2.67 (dd, J=16.5 and 4.3 Hz, 1H), 2.58 (dd, J=16.5 and 7.9 Hz, 1H), 1.27 (t, J=7.2 Hz, 3H). $^{13}$C NMR (75 MHz, $CDCl_3$): δ 171.7, 67.4, 61.0, 40.7, 14.1, 12.0.

EXAMPLE 2

Ethyl 3(S)-(tert-butyldimethylsilyloxy)-4-iodobutyrate (3)

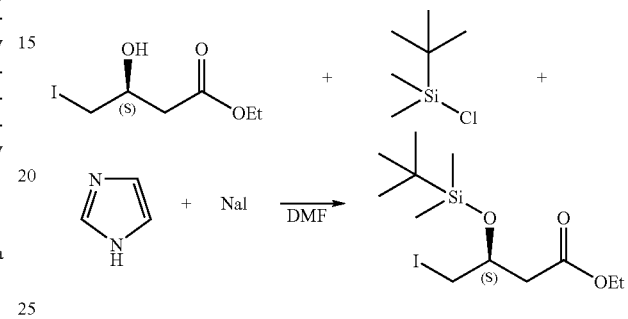

To a solution of imidazole (252.3 g, 7.36 mol) in dry DMF (7.6 L) are added ethyl 3(S)-hydroxy-4-iodobutyrate (2) (949.6 g, 3.68 mol, GC purity 85.9%) and anhydrous NaI (1106 g, 7.36 mol) under argon atmosphere at ambient temperature. The suspension is cooled to 0° C. and tert-butyl (chloro)dimethylsilane (838 g, 5.56 mol) is added portionwise. The reaction mixture is stirred at 0° C. for 1.5 hours followed by stirring for 15.5 hours from 0° C. to ambient temperature. Then the mixture is cooled to 0° C. and $H_2O$ (4.2 L) is added. After 2 hours of stirring additional amount of $H_2O$ (6.2 L) and saturated $Na_2S_2O_3$ solution (0.5 L) are added. The product is extracted with t-BuMeO. The combined organic layers are washed with water and dried ($MgSO_4$). Ether is removed completely under the reduced pressure (20 mbar) at 60° C. to produce a yellow oily residue. This residue is purified further by vacuum distillation (80-89° C. at 0.150-0.310 mbar) to give 1193.5 g (97%) of ethyl 3(S)-(tert-butyldimethylsilyloxy)-4-iodobutyrate (3) as a pale yellow oil (GC purity 96.1%). $^1$H NMR (300 MHz, $CDCl_3$): δ 4.13 (qd, J=7.2 and 2.1 Hz, 2H), 4.01 (m, 1H), 3.28 (dd, J=10.2 and 4.2 Hz, 1H), 3.24 (dd, J=10.2 and 6.0 Hz, 1H), 2.66 (dd, J=15.3 and 4.8 Hz, 1H), 2.51 (dd, J=15.3 and 7.2 Hz, 1H), 1.26 (t, J=7.2 Hz, 3H), 0.87 (s, 9H), 0.10 (s, 3H), 0.05 (s, 3H). $^{13}$C NMR (75 MHz, $CDCl_3$): δ 170.8, 68.3, 60.5, 42.5, 25.6, 17.9, 14.1, 12.9, −4.6, −5.0.

EXAMPLE 3

Ethyl 3(R)-(tert-butyldimethylsilyloxy)-5-hexenoate (4)

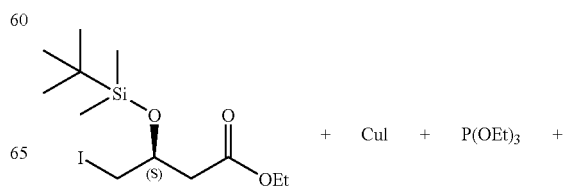

-continued

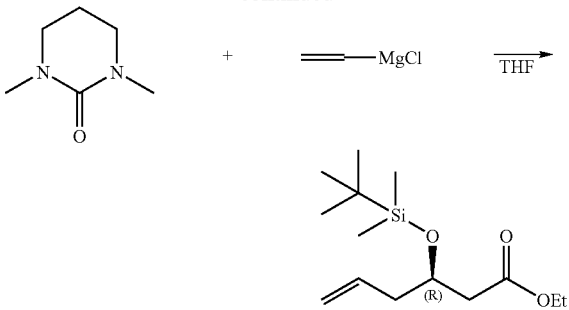

To a suspension of CuI (83.64 g, 437.0 mmol) in dry THF (875 mL), vinylmagnesium chloride (1.9 M in THF, 460.0 mL, 874.0 mmol) is added under argon atmosphere at 44 to −31° C. in 15 minutes under vigorous stirring. The resulting dark slurry is stirred for 15 minutes, and DMPU (112 g, 874.0 mmol) is added at 42° C. in one portion followed by the dropwise addition (5 minutes) of P(OEt)$_3$ (160.1 mL, 874.0 mmol) at 40° C. The resulting mixture is stirred for 30 minutes and a THF (220 mL) solution of (S)-ethyl 3-(tert-butyldimethylsilyloxy)-4-iodobutyrate (3) (162.7 g, 437.0 mmol) is added at −40 to −36° C. in 15 minutes. The stirring is continued for 1 hour at −40 to −35° C. before allowing the mixture to warm to 11° C. over a period of 3.5 hours. The reaction is quenched at −2° C. (saturated NH$_4$Cl, 1.0 L) and stirred at 10° C. for 30 minutes. The product is extracted with i-Pr$_2$O or t-BuMeO. Partial evaporation of the solvent under reduced pressure gives a yellow solution which is washed with 0.1 M H$_2$SO$_4$, water and dried (MgSO$_4$). Ether is removed completely under reduced pressure (15 mbar) at 80° C. to produce a yellow oily residue. This residue is purified further by vacuum distillation (64-72° C. at 0.10-0.44 mbar) to give 80.8 g (67.8%) of ethyl 3(R)-(tert-butyldimethylsilyloxy)-5-hexenoate (4) as a colorless oil (GC purity 96%). $^1$H NMR (300 MHz, CDCl$_3$): δ 5.81 (ddt, J=17.8, 9.6 and 7.2 Hz, 1H), 5.11-5.03 (m, 2H), 4.21 (quint., J=6.8 Hz, 1H), 4.12 (qt, J=7.1 and 1.5 Hz, 2H), 2.43 (d, J=7.1 Hz, 1H), 2.43 (d, J=5.4 Hz, 1H), 2.31-2.25 (m, 2H), 1.26 (t, J=7.2 Hz, 3H), 0.87 (s, 9H), 0.07 (s, 3H), 0.04 (s, 3H). $^{13}$C NMR (75 MHz, CDCl$_3$): δ 171.7, 134.1, 117.6, 68.9, 60.2, 42.1, 42.1, 25.7, 17.9, 14.1, −4.6, −5.0.

EXAMPLE 4

(R)-3-(tert-butyldimethylsilyloxy)-5-hexenoic acid (5)

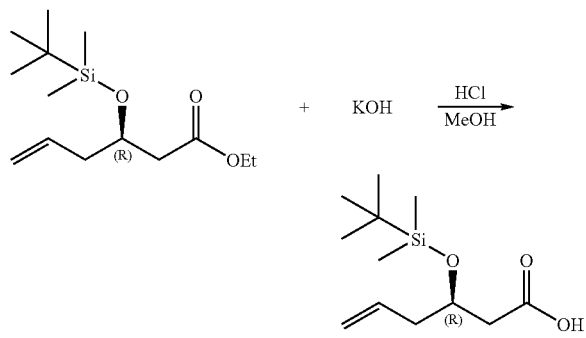

To a solution of ethyl 3(R)-(tert-butyldimethylsilyloxy)-5-hexenoate (4) (80.60 g, 295.8 mmol) in MeOH (500 mL) is added a 40% KOH solution (150 mL). The mixture is stirred for 2 hours at 40° C. After the mixture is cooled to ambient temperature and MeOH is removed under reduced pressure (20 mbar) at 42° C., the obtained brown solid is dissolved in H$_2$O (700 mL). The solution is washed with t-BuMeO (1×340 mL+3×215 mL) and then acidified with 4N HCl (222 mL) to pH=2. The yellow oil that separated from the water is extracted into t-BuMeO (6×110 mL). The combined organic layers are washed with water and dried (MgSO$_4$). Ether is removed completely under reduced pressure (15 mbar) at 40° C. to give an orange-red oily residue (68.2 g, 94.3%). This residue is filtered two times through a thin pad of silica using t-BuMeO as solvent to afford (R)-3-(tert-butyldimethylsilyloxy)-5-hexenoic acid (5) (67.1 g, 93%) as yellow oil (GC purity 97.3%). $^1$H NMR (300 MHz, CDCl$_3$): δ 11.03 (br s, 1H), 5.80 (ddt, J=17.8, 9.5 and 7.2 Hz, 1H), 5.13−5.11 (m, 1H), 5.08−5.06 (m, 1H), 4.20 (quint., J=6.5 Hz, 1H), 2.54 (dd, J=15.1 and 5.1 Hz, 1H), 2.46 (dd, J=15.1 and 7.1 Hz, 1H), 2.33−2.28 (m, 2H), 0.88 (s, 9H), 0.09 (s, 3H), 0.07 (s, 3H). $^{13}$C NMR (75 MHz, CDCl$_3$): δ 178.1, 133.8, 118.1, 68.8, 42.0, 41.8, 25.7, 17.9, −4.5, −5.0.

EXAMPLE 5

(4R,6S)-4-(tert-butyldimethylsilyloxy)-6-(iodomethyl)-tetrahydropyran-2-one (6a)

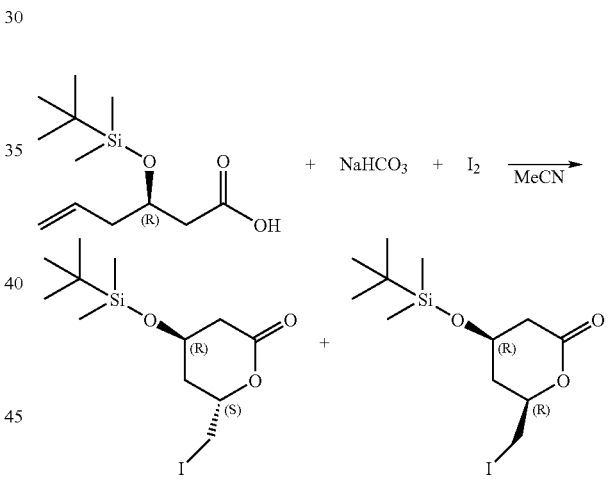

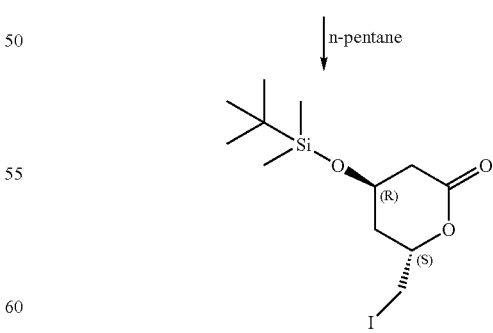

To a solution of (R)-3-(tert-butyldimethylsilyloxy)-5-hexenoic acid (5) (68.00 g, 278.2 mmol) in dry MeCN (950 mL) is added anhydrous NaHCO$_3$ (708.3 g, 8.347 mol) at ambient temperature. The stirred suspension is cooled to 0° C. Then iodine (212.9 g, 834.7 mmol) is added to the vigorously stirred suspension in one portion. The reaction mixture is stirred at 0° C. for 4 hours followed by the addition of t-BuMeO or i-Pr$_2$O (410 mL) and saturated Na$_2$S$_2$O$_3$ solution (820 mL). The organic layer is separated and the water phase was extracted additionally with t-BuMeO or i-Pr$_2$O (5×200 mL). The combined organic layers are dried (MgSO$_4$). Solvents are removed substantially under reduced pressure (20 mbar) at 40° C. to produce an orange oily residue. This residue is dissolved in t-BuMeO or i-Pr$_2$O (200 mL) and the solution is washed additionally with saturated Na$_2$S$_2$O$_3$ solution (2×100 mL) and water (2×100 mL). The organic layer is dried (MgSO$_4$). Solvent is removed completely under reduced pressure (20 mbar) at 50° C. to produce a yellow oily residue (99.96 g, 97%) which solidifies at temperatures below 10° C. to produce a 77:23 mixture of (4R,6S)-4-(tert-butyldimethylsilyloxy)-6-(iodomethyl)-tetrahydropyran-2-one (6a) and (4R,6R)-4-(tert-butyldimethylsilyloxy)-6-(iodomethyl)-tetrahydropyran-2-one (6b) as pale yellow solid. Raw mixture is dissolved in mobile phase (hexane and t-BuMeO) and at room temperature successively injected onto HPLC using normal phase silica column (PHENOMENEX 4.6×150 mm, d$_p$=5 μm) and eluted at isochratic conditions. Active fraction (whole peak) from preparative run is collected, and analysis on the same system showrf 97 area % of (6a) and 0.15% of (6b), with some other impurities present.

Alternatively to chromatographic purification this solid is recrystallized seven times from n-pentane to afford 43.6 g (42.6%) of (4R,6S)-4-(tert-butyldimethylsilyloxy)-6-(iodomethyl)-tetrahydropyran-2-one (6a) (d.e. 99.3%, HPLC) as colorless needles. M.p.=64° C. (DSC peak). $^1$H NMR (300 MHz, CDCl$_3$) δ: 4.60 (ddt, 1H, J=11.3, 5.0, 3.2 Hz, 6-H$_{ax}$), 4.35 (br quin, 1H, J=3.5 Hz, 4-H$_{eq}$), 3.40 (d, 2H, J=5.0 Hz, CH$_2$I), 2.59 (d, 2H, J=3.5 Hz, 3-CH$_2$), 2.10 (dddd, 1H, J=13.9, 3.9, 3.2, 1.7 Hz, 5-H$_{eq}$), 1.76 (ddd, 1H, J=13.7, 11.3, 2.1 Hz, 5-H$_{ax}$), 0.89 (s, 9H, SiC(CH$_3$)$_3$), 0.09, (s, 6H, Si(CH$_3$)$_2$). $^{13}$C NMR (75 MHz, CDCl$_3$) δ: 169.0, 73.9, 63.1, 38.7, 36.2, 25.5, 17.7, 8.6, −5.1, −5.1.

EXAMPLE 6

((2S,4R)-4-(tert-butyldimethylsilyloxy)-6-oxo-tetrahydro-2H-pyran-2-yl)methyl acetate (7)

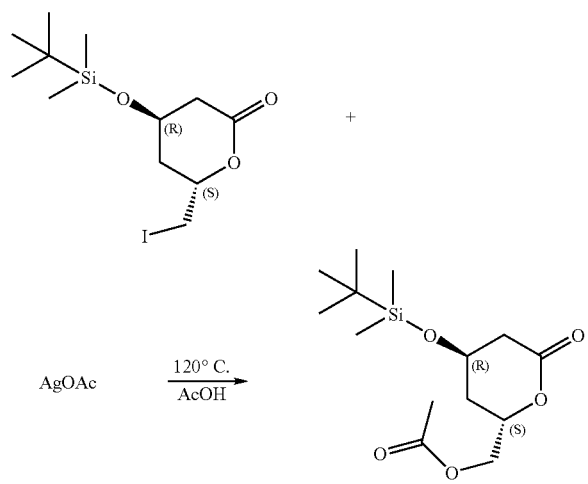

To the solution of (4R,6S)-4-(tert-butyldimethylsilyloxy)-6-(iodomethyl)-tetrahydropyran-2-one (6a) (40.00 g, 108.0 mmol) in AcOH (660 mL) is added AgOAc (20.03 g, 118.8 mmol). The resultant mixture is then heated at 125° C. for 6 hours. The reaction mixture is filtered through diatomite filter medium (Celite®). The obtained filtrate is evaporated to afford the residue. To this residue EtOAc (500 mL) and water (600 mL) are added. The organic layer is separated and the aqueous layer is washed again with EtOAc (5×150 mL). The combined organic layers are washed with water (4×300 mL), brine (5×300 mL) and dried over anhydrous MgSO$_4$, filtered and concentrated under the reduced pressure to afford 30.28 g (92.6%) of ((2S,4R)-4-(tert-butyldimethylsilyloxy)-6-oxo-tetrahydro-2H-pyran-2-yl)methyl acetate (7) as yellow oil (HPLC purity 98%). $^1$H NMR (300 MHz, CDCl$_3$): δ 4.93 (m, 1H), 4.37 (m, 1H), 4.30 (dd, J=12 Hz, J=3 Hz, 1H), 4.21 (dd, J=12 Hz, J=5 Hz, 1H), 2.62 (d, J=4 Hz, 2H), 2.11 (s, 3H), 1.84–1.80 (m, 2H), 0.89 (s, 9H), 0.09, 0.09 (2s, 6H). $^{13}$C NMR (75 MHz, CDCl$_3$): δ 170.4, 169.1, 73.3, 65.5, 63.0, 38.9, 32.2, 20.5, 17.7, −5.1, −5.2.

EXAMPLE 7

(4R,6S)-4-(tert-butyldimethylsilyloxy)-6-(hydroxymethyl)-tetrahydropyran-2-one (8)

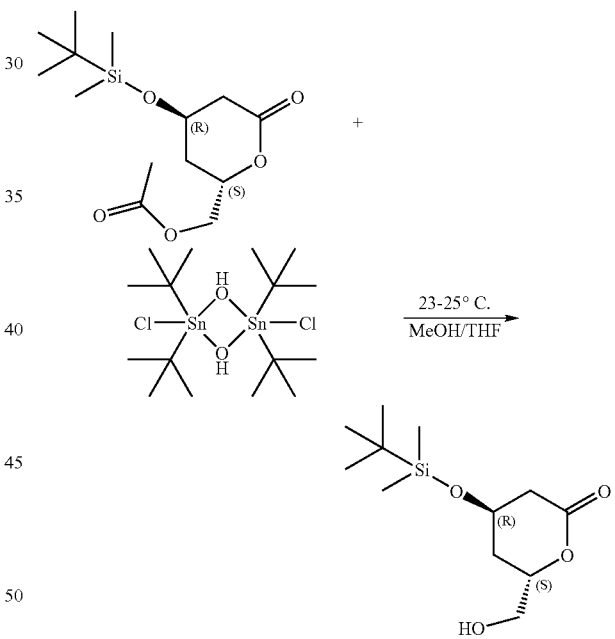

(2S,4R)-4-(tert-butyldimethylsilyloxy)-6-oxo-tetrahydro-2H-pyran-2-yl)methyl acetate (7) (8.36 g, 27.64 mmol) and [t-Bu$_2$SnOH(Cl)]$_2$ (1.577 g, 2.764 mmol) are dissolved in MeOH/THF mixture (280 mL). The reaction mixture is stirred at 23-25° C. for 27 h. The solvent is removed under reduced pressure and the remaining residue is purified by silica gel chromatography (elution with t-BuMeO/hexane mixture) to afford a crude product as white solid (5.59 g, 78%). Recrystallization from n-hexane affords (3.90 g, 54%) of (4R,6S)-4-(tert-butyldimethylsilyloxy)-6-(hydroxymethyl)-tetrahydro-pyran-2-one (8) as white needles. M.p.=102° C. (DSC peak). $^1$H NMR (300 MHz, CDCl$_3$) δ: 4.80 (m, 1H), 4.38 (m, 1H), 3.91 (dd, J=12 Hz, J=3 Hz, 1H), 3.66 (dd, J=12 Hz, J=5 Hz, 1H), 2.60 (d, J=4 Hz, 2H), 2.31

(bs, 1H), 1.97–1.75 (m, 2H), 0.88 (s, 9H), 0.09, 0.08 (2s, 6H). ¹³C NMR (75 MHz, CDCl₃) δ: 170.1, 76.8, 64.7, 63.4, 39.2, 31.9, 25.6, 17.9, −4.9, −5.0.

EXAMPLE 8

(2S,4R)-4-(tert-butyldimethylsilyloxy)-6-oxo-tetrahydro-2H-pyran-2-carbaldehyde (9)

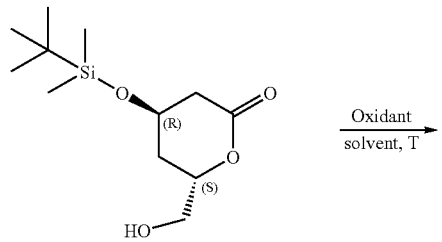

a) Dess-Martin periodinane or SIBX, CH₂Cl₂, or BMIMBF₄ r.t. or c) Swern oxidation, -30 to -80° C.

A mixture of (4R,6S)-4-(tert-butyldimethylsilyloxy)-6-(hydroxymethyl)-tetrahydropyran-2-one (8) (150 mg, 0.58 mmol) and Dess-Martin periodinane (380 mg, 0.86 mmol) in CH₂Cl₂ (15 mL) is stirred at ambient temperature for 3 hours. The mixture is diluted with t-BuMeO (20 mL), washed with saturated Na₂S₂O₃ solution, saturated NaHCO₃ solution, dried (MgSO₄) and concentrated to give 130 mg (87%) of crude (2S,4R)-4-(tert-butyldimethylsilyloxy)-6-oxo-tetrahydro-2H-pyran-2-carbaldehyde (9) which is used in the next step without further purification. ¹H NMR (300 MHz, CDCl₃) δ: 9.82 (s, 1H), 5.09 (dd, J=11 Hz, J=4 Hz, 1H), 4.38 (m, 1H), 2.67 (d, J=4 Hz, 2H), 2.18–2.10 (m, 1H), 1.91–1.81 (m, 1H), 0.89 (s, 9H), 0.09, (s, 6H). ¹³C NMR (75 MHz, CDCl₃) δ: 199.4, 168.0, 79.2, 62.9, 39.6, 31.4, 25.6, 17.9, −4.9. The hydrate form of (9) has following NMR spectra: ¹H NMR (300 MHz, THF-d₈) δ: 5.27 (d, J=6 Hz, 1H, OH), 5.19 (d, J=6 Hz, 1H, OH), 4.90–4.85 (m, 1H), 4.44–4.38 (m, 2H), 2.58 (dd, J=17 Hz, J=4 Hz, 1H), 2.44–2.36 (m, 1H), 1.92–1.87 (m, 2H), 0.91 (s, 9H), 0.10, (s, 6H). ¹³C NMR (75 MHz, THF-d₈) δ: 168.7, 91.7, 79.0, 65.1, 40.3, 31.0, 26.2, 18.7, −4.8, −4.8.

EXAMPLE 9

N-(5-((E)-2-((2S,4R)-4-(tert-butyldimethylsilyloxy)-6-oxo-tetrahydro-2H-pyran-2-yl)vinyl)-4-(4-fluorophenyl)-6-isopropylpyrimidin-2-yl)-N-methyl-methanesulfonamide (10)

EXAMPLE a)

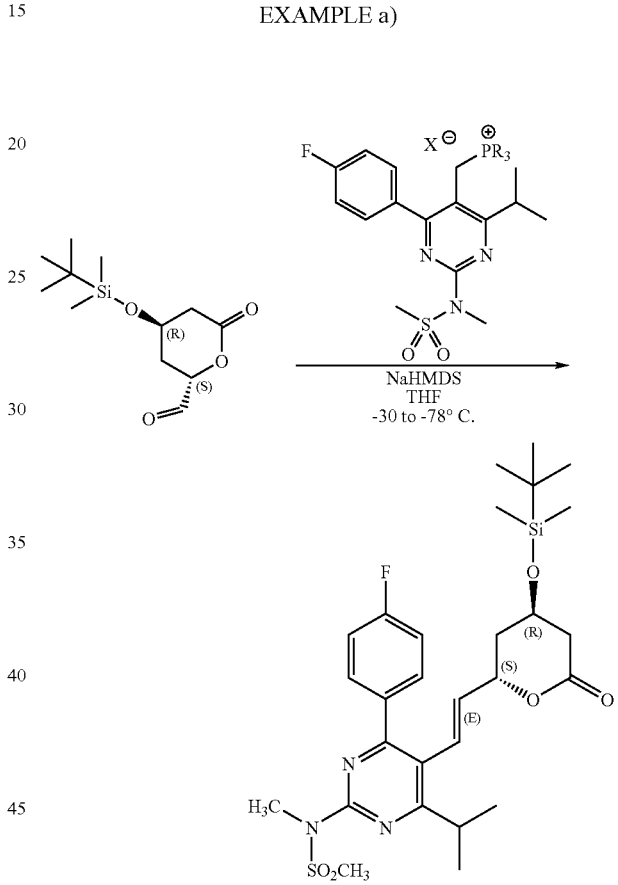

To a cold (−30° C.), stirred suspension of ((4-(4-fluorophenyl)-6-isopropyl-2-(N-methylmethylsulfonamido)pyrimidin-5-yl)methyl)triphenylphosphonium bromide (376 mg, 0.55 mmol) in dry tetrahydrofuran (10 mL) is added lithium hexamethyldisilazane in THF (0.42 mL of 1.33 M, 0.55 mmol). The reaction mixture is stirred for 30 min, cooled to −78° C., and treated with a solution of (2S,4R)-4-(tert-butyldimethylsilyloxy)-6-oxo-tetrahydro-2H-pyran-2-carbaldehyde (9) (130 mg, 0.50 mmol) in 5 mL of tetrahydrofuran. After 60 min, the solution is warmed to ambient temperature, stirred for 10 min, and treated with saturated ammonium chloride solution. The aqueous phase is extracted with t-BuMeO (2×10 mL), and the combined organic layers dried and concentrated. The residue is purified by silica gel chromatography (elution with t-BuMeO/hexane mixture) to give 190 mg (65%) of N-(5-((E)-2-((2S,4R)-4-(tert-butyldimethylsilyloxy)-6-oxo-tetrahydro-2H-pyran-2-yl)vinyl)-4-(4- fluorophenyl)-6-isopropylpyrimidin-2-yl)-N-methyl-methanesulfonamide (10) as white amorphous solid.

EXAMPLE b)

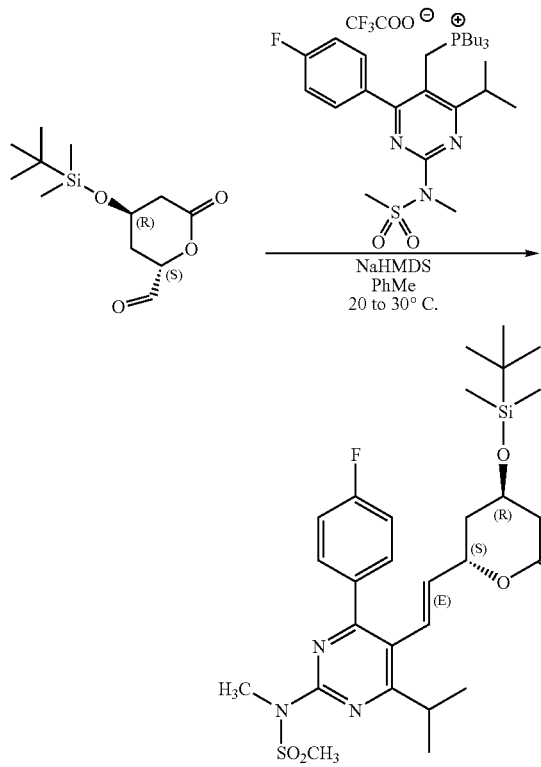

To a stirred suspension of ((4-(4-fluorophenyl)-6-isopropyl-2-(N-methylmethyl-sulfonamido)pyrimidin-5-yl)methyl)tributylphosphonium 2,2,2-trifluoro-acetate (260 mg, 0.4 mmol) at room temperature in dry toluene (4 mL) is added sodium hexamethyldisilazane in toluene (0.67 mL of 0.6 M, 0.4 mmol) portionwise in 10 minutes. The reaction mixture is stirred for 60 min and treated at room temperature with a solution of (2S,4R)-4-(tert-butyldimethylsilyloxy)-6-oxo-tetrahydro-2H-pyran-2-carbaldehyde (9) (105 mg, 0.40 mmol) in 13 mL of dry toluene. After 24 hours of stirring at room temperature the solution is treated with saturated ammonium chloride solution or water. The aqueous phase is extracted with t-BuMeO (2×10 mL), and the combined organic layers dried and concentrated. The residue is purified by silica gel chromatography (elution with t-BuMeO/hexane mixture) to give 104 mg (45%) of N-(5-((E)-2-((2S,4R)-4-(tert-butyldimethylsilyloxy)-6-oxo-tetrahydro-2H-pyran-2-yl)vinyl)-4-(4-fluorophenyl)-6-isopropylpyrimidin-2-yl)-N-methylmethanesulfonamide (10) as white amorphous solid.

$^1$H NMR (300 MHz, CDCl$_3$) δ: 7.62 (dd, J=9 Hz, J=5 Hz, 2H), 7.09 (t, J=9 Hz, 2H), 6.69 (dd, J=16 Hz, J=1 Hz, 1H), 5.49 (dd, J=16 Hz, J=6 Hz, 1H), 5.22–5.16 (m, 1H), 4.29–4.27 (m, 1H), 3.56 (s, 3H), 3.50 (s, 3H), 3.32 (septet, 1H), 2.61–2.59 (m, 2H), 1.80-1.73 (m, 1H), 1.64–1.54 (m, 1H), 1.26 (d, J=7 Hz, 6H), 0.87 (s, 9H), 0.07, 0.06 (2s, 6H). $^{13}$C NMR (75 MHz, CDCl$_3$) δ: 174.9, 169.5, 163.5, 163.2 (d, $J_{C-F}$=250 Hz), 157.4, 134.7, 134.1 (d, $J_{C-F}$=3 Hz), 132.0 (d, $J_{C-F}$=8 Hz), 125.3, 120.5, 115.0 (d, $J_{C-F}$=22 Hz), 75.3, 63.2, 42.3, 39.2, 36.2, 33.0, 32.1, 25.5, 21.5, 17.8, −5.0, −5.0.

EXAMPLE 10

Calcium salt of (3R,5S,E)-7-(4-(4-fluorophenyl)-6-isopropyl-2-(N-methylmethylsulfonamido)pyrimidin-5-yl)-3,5-dihydroxyhept-6-enoic acid (11)

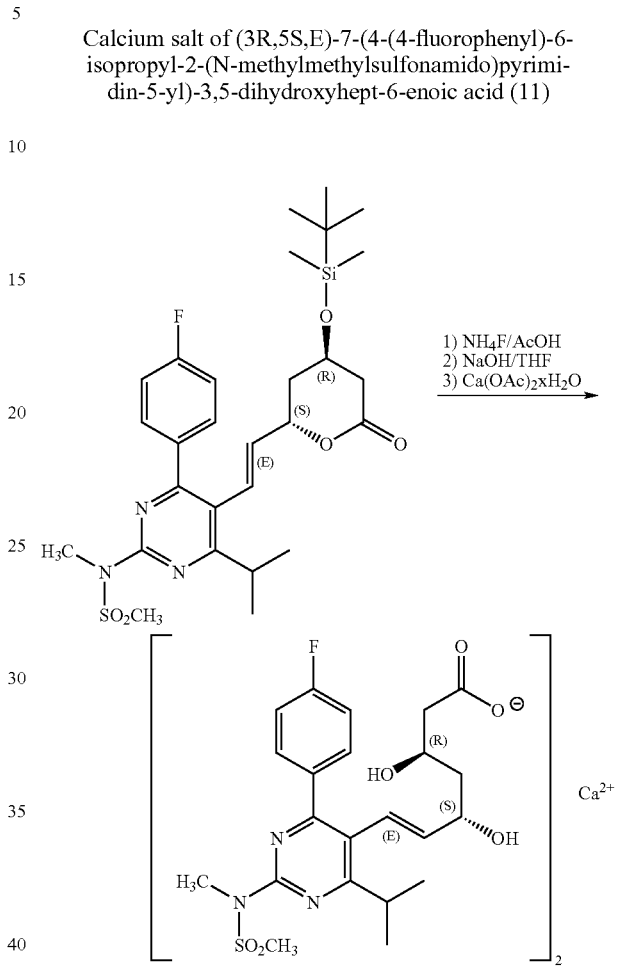

To a stirred solution of N-(5-((E)-2-((2S,4R)-4-(tert-butyldimethylsilyloxy)-6-oxo-tetrahydro-2H-pyran-2-yl)vinyl)-4-(4-fluorophenyl)-6-isopropylpyrimidin-2-yl)-N-methylmethanesulfonamide (10) (190 mg, 0.33 mmol) in 3 mL of anhydrous tetrahydrofuran is added a solution of ammonium fluoride (73 mg, 1.97 mmol)/AcOH (2 mL) in THF. The reaction mixture is warmed to 60° C., stirred for 5 h, treated with 3 mL of aqueous ammonium chloride solution, and extracted several times with t-BuMeO. The combined organic layers are washed with water, dried and concentrated. The residue is dissolved in 3 mL of a 4:1 mixture of THF/H$_2$O. The clear solution is warmed to 30° C. and 8.0 M NaOH (0.044 mL, 0.35 mmol) is added portionwise. The reaction mixture is stirred at 30° C. for 2 hours giving a clear yellow solution. Then THF is removed completely under reduced pressure (20 mbar) at 40° C. The remaining water solution is diluted with H$_2$O to 1.5 mL and washed with AcOEt (2×1 mL). After separation from the organic layer aqueous phase is distilled under reduced pressure (20 mbar) at 40° C. to completely remove the dissolved AcOEt. The remaining clear solution of sodium rosuvastatinate (1.3 mL) is diluted with H$_2$O to 1.5 mL and warmed to 40° C. To a vigorously stirring solution of sodium rosuvastatinate is added dropwise Ca(OAc)$_2$×H$_2$O (44 mg, 0.25 mmol in 0.3 mL of H$_2$O) over 5 minutes at 40° C. to precipitate rosuvastatin calcium. After the complete addition, the suspension is stirred further for 30 minutes at 40° C. The white precipitate is filtered off. Then a wet white solid is suspended in H₂O (1 mL) and vigorously stirred for 1 hour at 20° C. The undissolved precipitate is collected by filtration, washed with H₂O (1 mL) and dried in vacuum at 40° C. to give 143 mg (87%) of rosuvastatin calcium salt (11) as white powder.

The invention claimed is:

1. A process for manufacturing rosuvastatin, characterized in that it comprises steps:

a) (optionally) reacting alkyl 3(S)-hydroxy-4-chlorobutyrate of formula I,

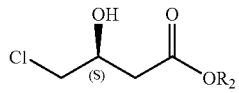

wherein $R_2$ is an optionally substituted $C_1$-$C_8$ alkyl or $C_5$-$C_7$ cycloalkyl, or alternatively, —COOR₂ may also form an amide of formula —CONR$_a$,R$_b$, where R$_a$ and R$_b$ may independently be H, an optionally substituted $C_1$-$C_8$ alkyl or $C_5$-$C_7$ cycloalkyl, aryl or can together with N form a heterocycle with an iodide to give an alkyl 3(S)-hydroxy-4-iodobutyrate of formula II

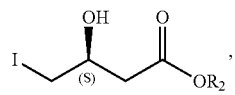

wherein $R_2$ is as above;

b) (optionally) protecting the compound of formula II to give a protected derivative of formula III,

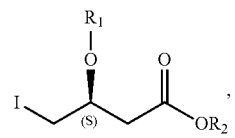

wherein $R_1$ and $R_2$ are as above;

c) reacting the compound of formula III with vinylmagnesium halide in presence of copper(I) halide and phosphite derivative with formula:

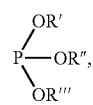

where each of R', R", and R'" are same or different $C_1$-$C_4$ alkyl, $C_5$-$C_7$ cycloalkyl, or aryl which may be optionally substituted to give an alkene of formula IV

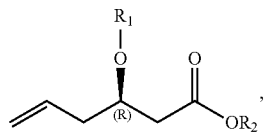

wherein $R_1$ and $R_2$ are as above;

d) hydrolyzing the compound of formula IV to give compound of formula V

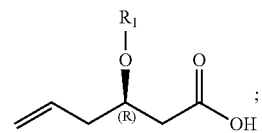

e) reacting compound of formula V, wherein $R_1$ is as above, with a source of halogen in the presence of NaHCO₃ to give compound of formula VI;

f) (optionally) separating the mixture of diastereoisomers obtained in previous step to obtain compound of formula VIa

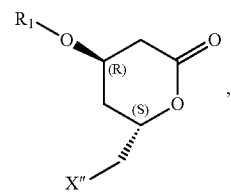

wherein X" is halo and $R_1$ as above;

g) converting the compound of formula VIa into compound of formula VII,

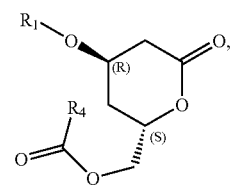

wherein $R_1$ is as above and $R_4$ is selected from (optionally halo or alkoxy or aryloxy substituted) $C_1$-$C_4$ alkyl;

h) converting compound of formula VII in compound of formula VIII

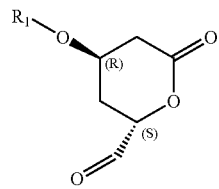

wherein $R_1$ is as above;

i) converting the compound of formula VIII by oxidation into compound of formula IX,

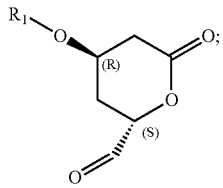

wherein $R_1$ is as above;

j) reacting said compound of formula IX with the compound of formula

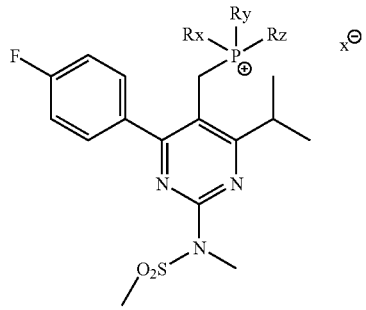

wherein Rx, Ry, and Rz are the same or different and are selected from optionally substituted $C_1$-$C_8$ alkyl or $C_3$-$C_6$ cycloalkyl or $C_1$-$C_8$ alkenyl or $C_5$-$C_6$ cycloalkenyl or aryl, $X^-$ is anion; and k) removing the protecting group $R_1$, optionally purifying and converting the obtained compound into calcium salt.

2. A process according to claim 1, wherein the anion $X^-$ is a halide or alkanoate.

3. A method for using an intermediate IX for the synthesis of statins, wherein the intermediate IX includes

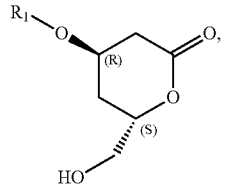

the method comprising the steps of preparing the intermediate IX from intermediate of formula VIa

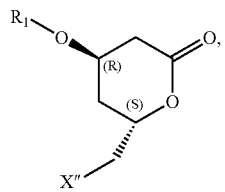

wherein X" is halo, arylsulfonyl or alkylsulfonyl and $R_1$ is a protecting group.

4. A method for using an intermediate for the synthesis of statins, wherein the intermediate is of the formula

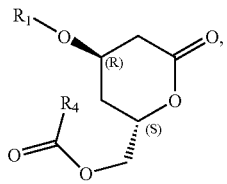

wherein $R_1$ is an optionally substituted $C_1$-$C_8$ trialkylsilyl, $C_1$-$C_8$ dialkylarylsilyl, $C_1$-$C_8$ alkyldiarylsilyl, where alkyls may be same or different and $R_4$ is (optionally halo, alkyl, aryl, alkyloxy or aryloxy substituted) $C_1$-$C_4$ alkyl.

* * * * *